(12) United States Patent
Oka et al.

(10) Patent No.: US 12,357,300 B2
(45) Date of Patent: Jul. 15, 2025

(54) NEEDLE HOLDER FOR ENDOSCOPE AND OPERATING METHOD OF SUTURE NEEDLE

(71) Applicant: OLYMPUS CORPORATION, Hachioji (JP)

(72) Inventors: Kosuke Oka, Tokyo (JP); Masatoshi Tonomura, Koganei (JP); Kunihide Kaji, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 550 days.

(21) Appl. No.: 17/683,771

(22) Filed: Mar. 1, 2022

(65) Prior Publication Data
US 2022/0218330 A1  Jul. 14, 2022

Related U.S. Application Data

(63) Continuation of application No. PCT/JP2019/041694, filed on Oct. 24, 2019.

(51) Int. Cl.
*A61B 17/062* (2006.01)
*A61B 17/00* (2006.01)
*A61B 17/04* (2006.01)

(52) U.S. Cl.
CPC ........ *A61B 17/062* (2013.01); *A61B 17/0469* (2013.01); *A61B 2017/00818* (2013.01); *A61B 2017/00862* (2013.01)

(58) Field of Classification Search
CPC .............. A61B 17/062; A61B 17/0469; A61B 2017/00818; A61B 2017/00862
See application file for complete search history.

(56) References Cited

U.S. PATENT DOCUMENTS 5,628,757 A    5/1997  Hasson
2010/0057108 A1*  3/2010  Spivey ............. A61B 17/06066
                                                 606/144

(Continued)

FOREIGN PATENT DOCUMENTS

EP    3165175 A1    5/2017
JP    4481052 B2    6/2010

(Continued)

OTHER PUBLICATIONS

Jan. 21, 2020 International Search Report issued in International Patent Application No. PCT/JP2019/041694.

*Primary Examiner* — Shaun L David
*Assistant Examiner* — Rachael L Geiger
(74) *Attorney, Agent, or Firm* — Oliff PLC

(57) ABSTRACT

A needle holder includes a sheath, a grasper capable of grasping a target object, an operation portion capable of opening and closing the grasper, and an operation wire. The operation portion includes a main body, a slider, and an elastic member that is elastically deformable depending on an opening and closing position of the grasper. The slider is connected to the grasper via the operation wire. The grasper can release grasping of the target object and can grasp the target object with a first grasping force in response to an operation of moving the slider against a restoring force of the elastic member. The grasper can grasp the target object with a second grasping force smaller than the first grasping force when the restoring force of the elastic member and tension of the operation wire are balanced.

20 Claims, 20 Drawing Sheets

(56) References Cited

U.S. PATENT DOCUMENTS

2012/0123471 A1* 5/2012 Woodard, Jr. ... A61B 17/06004
606/223
2017/0095249 A1* 4/2017 Ichikawa ........... A61B 17/0625

FOREIGN PATENT DOCUMENTS

| WO | 2016/002932 A1 | 1/2016 |
| WO | 2017/145337 A1 | 8/2017 |

* cited by examiner

NEEDLE HOLDER FOR ENDOSCOPE AND OPERATING METHOD OF SUTURE NEEDLE

This application is a continuation application of International Patent Application No. PCT/JP2019/041694 filed on Oct. 24, 2019, the content of which is incorporated herein by reference in its entirety.

The present disclosure relates to a needle holder for an endoscope and an operating method of a suture needle.

BACKGROUND

In the related art, a needle holder for an endoscope that grasps and moves a suture needle when performing a surgery on a part in a body cavity under the observation by an endoscope is known.

For example, a surgical grasper that grasps a suture needle is known. The surgical grasper has a grasper at a distal end of a rigid shaft. The grasper can adjust a force of grasping an object to be grasped. The direction or position of the suture needle can be changed to a desired direction or position without a need for the grasper to regrasp the suture needle.

SUMMARY

A needle holder for an endoscope including a sheath having a longitudinal axis; a grasper capable of grasping a target object; an operation portion capable of opening and closing the grasper; and an operation wire extending along the longitudinal axis of the sheath. The operation portion includes: a main body; a slider slidably attached to the main body; and an elastic member that is elastically deformable depending on an opening and closing position of the grasper. The slider is connected to the grasper via the operation wire. The grasper can release grasping of the target object and can grasp the target object with a first grasping force by moving the slider against a restoring force of the elastic member. The grasper can grasp the target object with a second grasping force smaller than the first grasping force when the restoring force of the elastic member and a tension of the operation wire are balanced.

An operating method of a suture needle includes: introducing a suture needle into a luminal organ through a natural opening; and changing a direction of a tip of the suture needle while pressing a part of the suture needle positioned inside the luminal organ against a digestive wall.

DETAILED DESCRIPTION OF EXEMPLARY EMBODIMENTS

Figure 1:
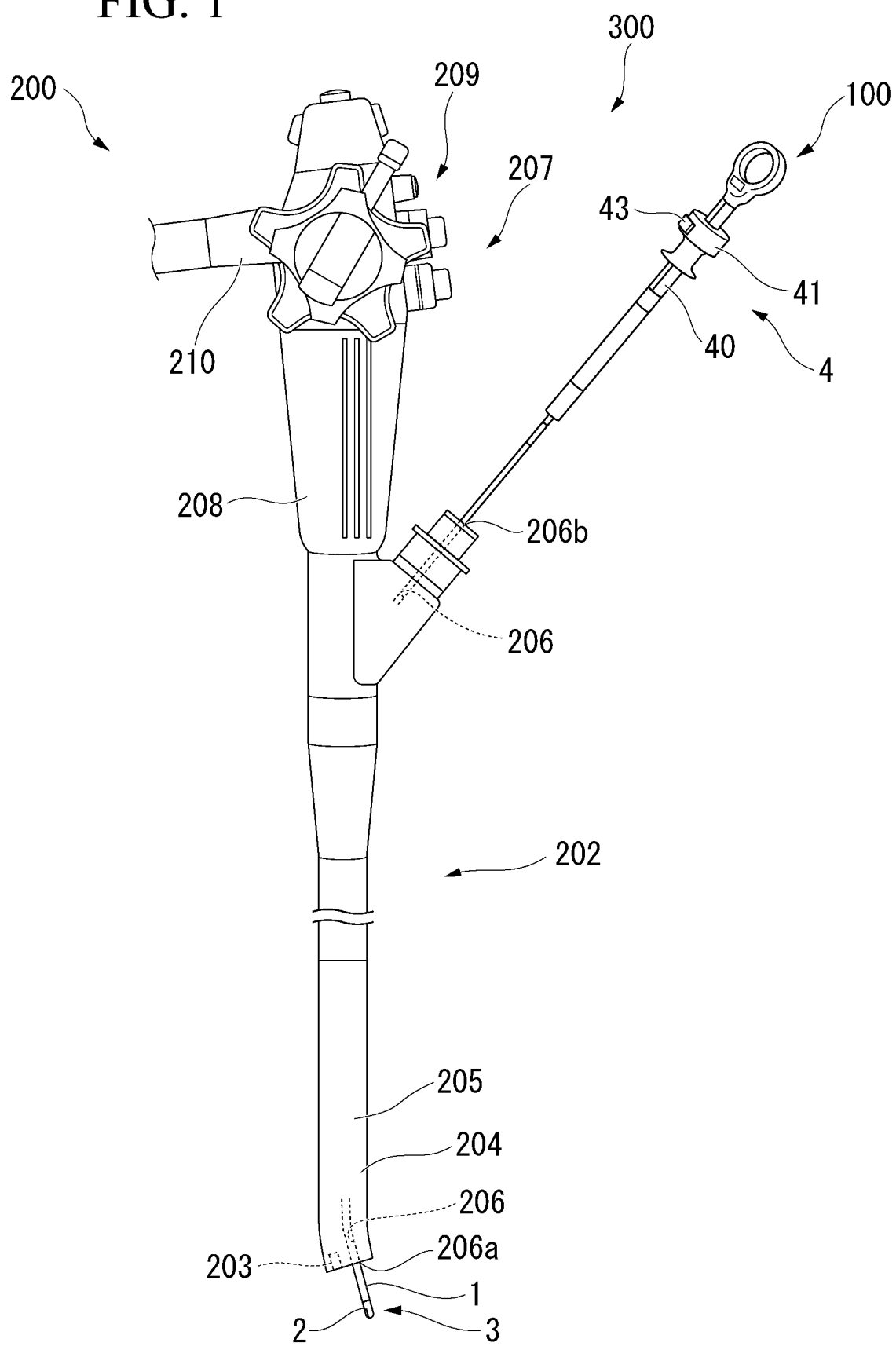
FIG. 1 is an overall view of a treatment system including a needle holder according to an exemplary embodiment.

A needle holder for an endoscope (hereinafter, referred to as a "needle holder") 100 according to an exemplary embodiment of the present disclosure will be described with reference to FIGS. 1 to 18. FIG. 1 is an overall view of a treatment system 300 including the needle holder 100 according to the present embodiment.

[Treatment System 300]

As shown in FIG. 1, the treatment system 300 includes a flexible endoscope 200 and the needle holder 100. The needle holder 100 is used by being inserted into the flexible endoscope 200.

[Flexible Endoscope 200]

As shown in FIG. 1, the flexible endoscope 200 includes an insertion portion 202 and an operation portion 207. The insertion portion 202 is inserted into a body from a distal end. The operation portion 207 is attached to a proximal end of the insertion portion 202.

The insertion portion 202 has an imaging portion 203, an active bending portion 204, and a flexible portion 205. The imaging portion 203, the active bending portion 204, and the flexible portion 205 are disposed in this order from the distal end of the insertion portion 202. A channel 206 for inserting the needle holder 100 is provided inside the insertion portion 202. A distal end opening portion 206a of the channel 206 is provided in the distal end of the insertion portion 202.

The imaging portion 203 includes, for example, CCD or CMOS, and is configured to image a part, which is a treatment target. The imaging portion 203 is configured to image a grasper 3 of the needle holder 100, which is to be described later, in a state where the needle holder 100 protrudes from the distal end opening portion 206a of the channel 206. The active bending portion 204 can be positively bent in response to an operation of the operation portion 207 by an operator. The flexible portion 205 is a tubular part having flexibility.

The operation portion 207 is connected to the flexible portion 205. The operation portion 207 has a grip 208, an input portion 209, a proximal end opening portion 206b of the channel 206, and a universal cord 210. The grip 208 is a part grasped by the operator. The input portion 209 receives an operation input for bending the active bending portion 204. The universal cord 210 outputs an image captured by the imaging portion 203 to the outside. The universal cord 210 is configured to be connected to a display device such as a liquid crystal device via an image processing device such as a processor.

[Needle Holder 100]

Figure 2:
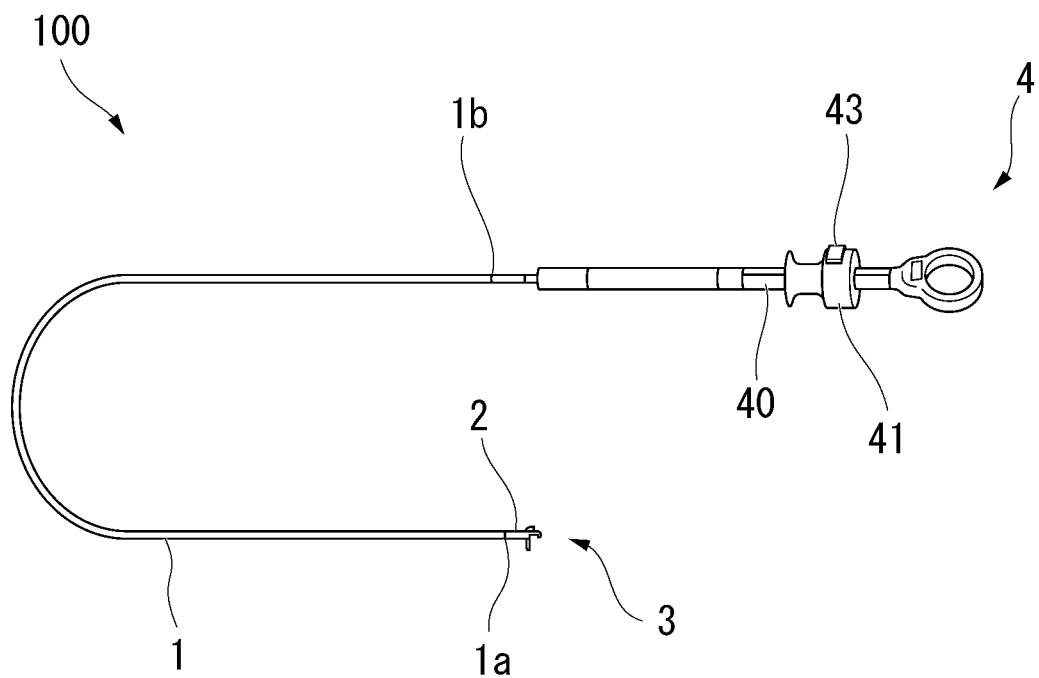
FIG. 2 is an overall view showing the needle holder.

FIG. 2 is an overall view showing the needle holder 100.

The needle holder 100 has a sheath 1, a hard portion 2, the grasper 3, an operation portion 4, and an operation wire 5 inserted through the sheath 1.

The sheath 1 is an elongated member that has flexibility and extends from a distal end 1a to a proximal end 1b. As shown in FIG. 1, the sheath 1 has an outer diameter allowing the sheath to be inserted into the channel 206 of the flexible endoscope 200. In a state where the sheath 1 is inserted in the channel 206, the distal end 1a of the sheath 1 is capable of protruding from and retracting to the distal end opening portion 206a of the channel 206. The distal end 1a of the sheath 1 can enter an imaging field view of the imaging portion 203 of the flexible endoscope 200, and is imaged by the imaging portion 203.

As shown in FIG. 2, the hard portion 2 is provided at the distal end 1a of the sheath 1. The hard portion 2 is formed of a hard material such as stainless steel (SUS). The grasper 3 is provided at the hard portion 2. The operation portion 4 is provided at the proximal end 1b of the sheath 1.

Figure 3:
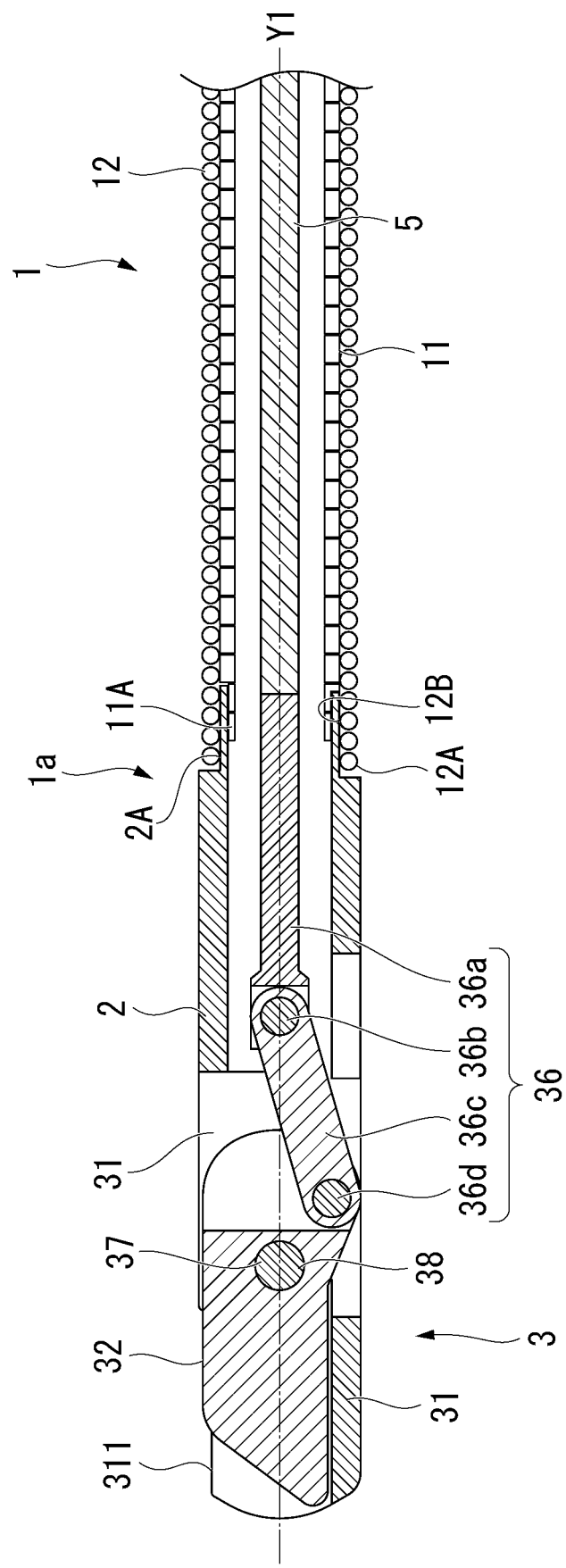
FIG. 3 is a cross sectional view of a cross section of a distal end of a sheath of the needle holder, which is horizontal to an axial direction.

FIG. 3 is a cross sectional view of the distal end 1a of the sheath 1.

The sheath 1 is a member endoscopically inserted into a body cavity, and has a first coil sheath 11 through which the operation wire 5 is inserted and a second coil sheath 12 through which the first coil sheath 11 is inserted. Without being limited to a coil sheath, the first coil sheath 11 may be a resin tube excellent in compression resistance such as PEEK.

The first coil sheath 11 is a so-called single-strand coil sheath formed by tightly winding one metal wire in a loop shape, has compression resistance to the inserted operation wire 5, and suitably transmits an opening and closing operation of the grasper 3 to the grasper 3 via the operation portion 4.

The second coil sheath 12 is a so-called multi-strand coil sheath formed by arranging a plurality of metal wires in a radial direction and tightly winding in a loop shape and suitably transmits an operation for rotating the grasper 3 to the grasper 3. The number of metal wires of the second coil sheath 12 may be determined as appropriate.

Although an example in which the first coil sheath 11 is formed by a metal wire of which a cross section metal wire is rectangular and the second coil sheath 12 is formed by a metal wire of which a cross section is circular has been described in the present embodiment shown in FIG. 3, the shapes of the cross sections of the metal wires are not limited thereto, and may be selected as appropriate according to a design value of the sheath 1.

As shown in FIG. 3, a region having a predetermined length from a distal end 12A of the second coil sheath 12 is processed to have a flat inner peripheral surface 12B through cutting or the like. A proximal end side of the hard portion 2 is formed in a tubular shape, and has an outer surface. The outer surface 2A is connected and fixed to the inner peripheral surface 12B of the second coil sheath 12. The inner peripheral surface 12B of the second coil sheath 12 and the outer surface 2A on the proximal end side of the hard portion 2 are fixed to each other through laser welding or brazing or the like.

A distal end 11A of the first coil sheath 11 is fixed to the proximal end of the hard portion 2 through laser welding or brazing or the like.

The distal end 12A of the second coil sheath 12 is fixed to the outer surface 2A of the hard portion 2. The distal end 12A of the second coil sheath 12 cannot rotate about an axis thereof with respect to the hard portion 2, and cannot move in an axial direction relatively to the first coil sheath 11.

A connection form between the hard portion 2 and the sheath 1 is not particularly limited to the description made above. For example, a configuration where in the proximal end part of the hard portion 2 formed in a tubular shape, the second coil sheath 12 is fixed to an outer surface, and the first coil sheath 11 is fixed to an inner surface may be adopted. In addition, the shape of a part of the hard portion 2, to which the sheath 1 is fixed, may not be tubular.

Figure 4:
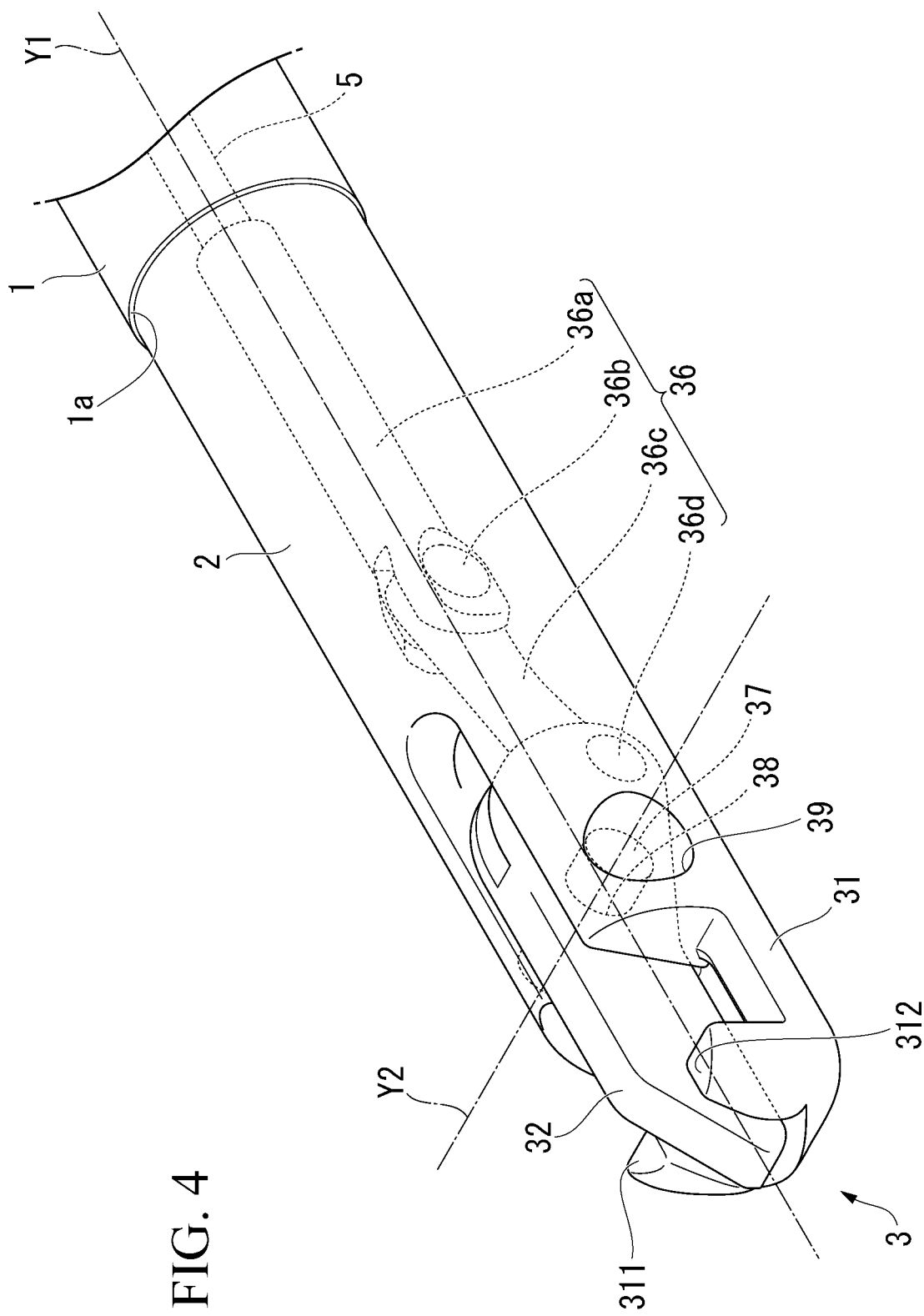
FIG. 4 is a perspective view showing a grasper of the needle holder.
Figure 5:
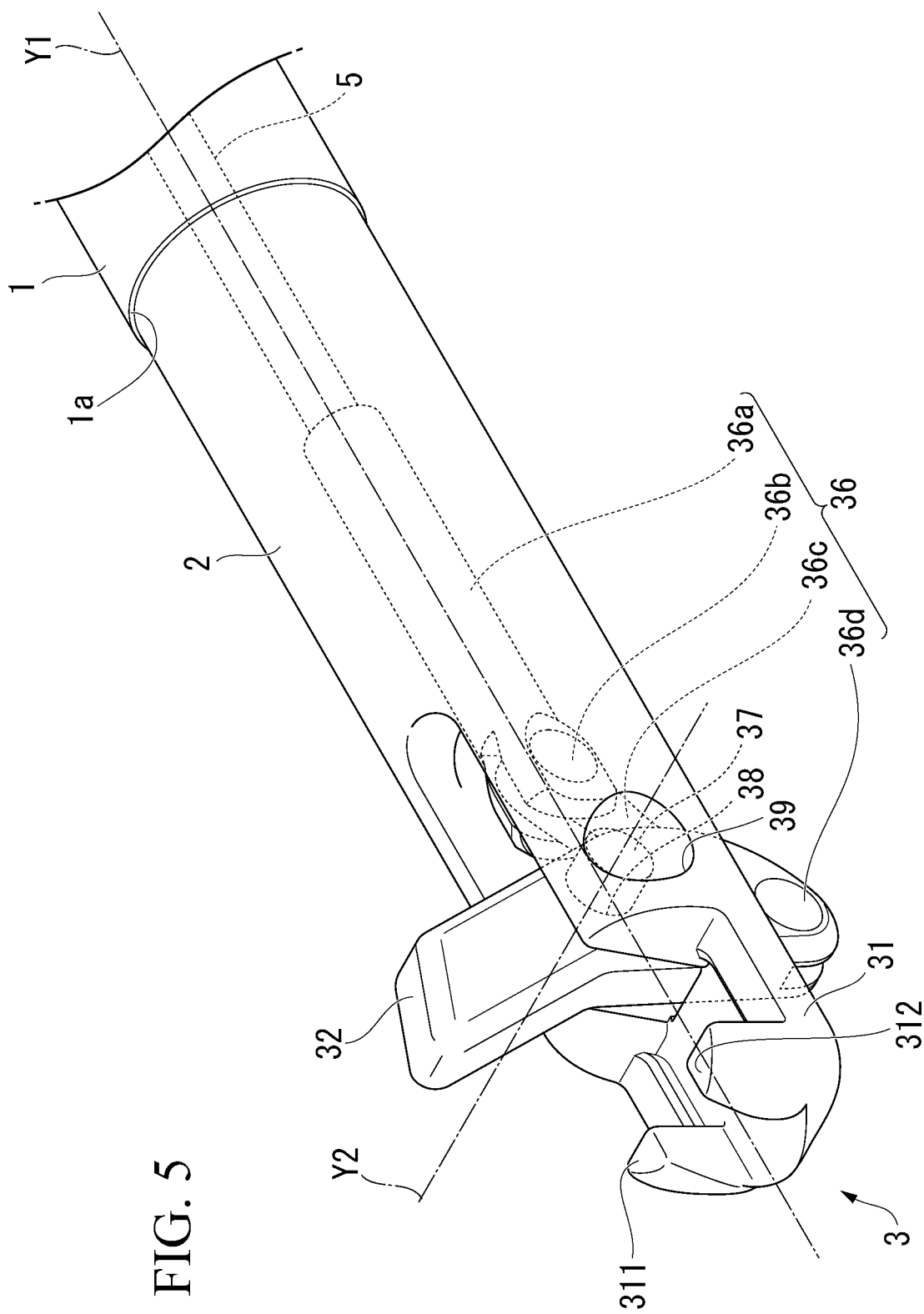
FIG. 5 is a perspective view showing the grasper of the needle holder.

FIGS. 4 and 5 are perspective views showing the grasper 3 of the needle holder 100.

The grasper 3 has a first grasp member 31, a second grasp member 32, and a link mechanism 36. The first grasp member 31 and the second grasp member 32 are configured to be openable and closable. FIG. 4 shows a state where the first grasp member 31 and the second grasp member 32 are closed. FIG. 5 shows a state where the first grasp member 31 and the second grasp member 32 are opened.

The first grasp member 31 is a part of a distal end portion of the hard portion 2. The first grasp member 31 extends along a longitudinal axis Y1 of the sheath 1. In the needle holder 100 of the present embodiment, the first grasp member 31 and the hard portion 2 are integrally molded.

The second grasp member 32 is connected to the hard portion 2 so as to be openable and closable with respect to the first grasp member 31. Specifically, for example, as a connecting shaft 37 is inserted into a through-hole 38 formed in the second grasp member 32 and a through-hole 39 formed in the hard portion 2, the second grasp member 32 is connected to the hard portion 2 so as to be movable rotationally. The second grasp member 32 is movable rotationally about a longitudinal axis Y2 of the connecting shaft 37.

The first grasp member 31 has a first protrusion portion 311 and a second protrusion portion 312. The first protrusion portion 311 and the second protrusion portion 312 are provided at a distal end portion of the first grasp member 31, and protrude in a direction intersecting the longitudinal axis (central axis) Y1. The first protrusion portion 311 and the second protrusion portion 312 are provided as a pair with the longitudinal axis Y1 of the sheath 1 interposed therebetween, and a distal end portion of the second grasp member 32 is positioned between the first protrusion portion 311 and the second protrusion portion 312 in a state where the first grasp member 31 and the second grasp member 32 are closed.

The link mechanism 36 is configured by a first link member 36a, a first joint member 36b, a second link member 36c, and a second joint member 36d. The first link member 36a is connected to the second link member 36c by the first joint member 36b. The second link member 36c is connected to the second grasp member 32 by the second joint member 36d.

Figure 6:
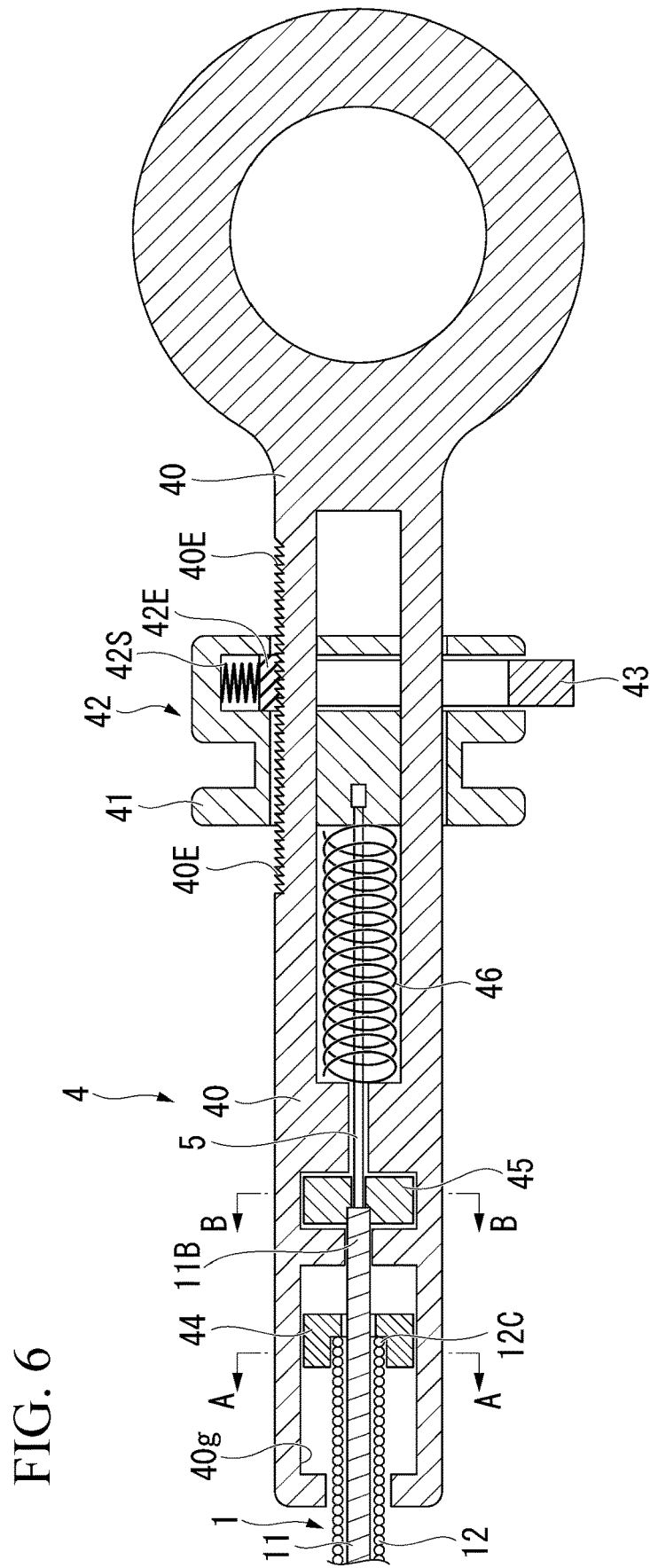
FIG. 6 is an enlarged cross sectional view of a cross section of a connection part between an operation portion and the sheath of the needle holder, which is horizontal to the axial direction.

FIG. 6 is an enlarged cross sectional view of a connection part between the operation portion (handle) 4 and the sheath 1.

The operation portion 4 has a main body 40, a slider 41, a fixing mechanism 42, a release button 43, a sliding member (key) 44, a locking member (disk) 45, and an elastic member 46.

A proximal end 12C of the second coil sheath 12 is fixed to the sliding member 44 inside the main body 40. A proximal end 11B of the first coil sheath 11 extending from the second coil sheath 12 is fixed to the locking member 45. The operation wire 5 extending from the first coil sheath 11 is connected to the slider 41 through the inside of the main body 40.

The slider 41 is connected to the main body 40 so as to be advanceable and retractable, and is advanceable and retractable along an axial direction of the main body 40.

The fixing mechanism 42 is a ratchet mechanism provided at the slider 41, and has a spring 42S and an engaging portion (claw) 42E. Although the slider 41 is allowed to retract along the axial direction of the main body 40 with respect to the main body 40, the fixing mechanism 42 does not allow advancement.

The engaging portion 42E of the fixing mechanism 42 engages with an engaged portion (ratchet tooth) 40E provided at the main body 40 through a restoring force of the spring 42S. In a case where the engaging portion 42E and the engaged portion 40E are engaged with each other, the slider 41 cannot advance with respect to the main body 40. On the other hand, even in a case where the engaging portion 42E and the engaged portion 40E are engaged with each other, the slider 41 can retract with respect to the main body 40.

The release button 43 is a button for releasing engagement between the engaging portion 42E and the engaged portion 40E by being pressed. A surgeon can advance the slider 41 along the axial direction of the main body 40 with respect to the main body 40 only in a case where the release button 43 is pressed. That is, since engagement (connection) between the engaging portion 42E and the engaged portion 40E is released by pushing the release button 43, the slider 41 can be advanced along the axial direction of the main body 40 with respect to the main body 40.

Figure 7:
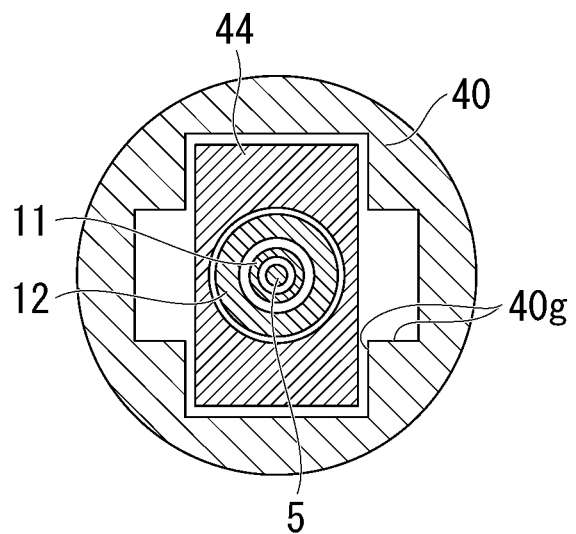
FIG. 7 is a cross sectional view taken along line A-A of FIG. 6.

FIG. 7 is cross sectional view taken along line A-A of FIG. 6.

The sliding member 44 is a member that slides inside the main body 40, and has a through-hole through which the first coil sheath 11 is inserted. Since a cross sectional shape of the sliding member 44 in a width direction of the main body 40 is a substantially oblong, the sliding member 44 is caught in a slide groove 40g when the main body 40 is rotated about an axis. Therefore, also the sliding member 44 and the second coil sheath 12 rotate about the axis together with the main body 40.

The sliding member 44 is slidable inside the slide groove 40g provided to extend in a longitudinal direction inside the main body 40. That is, the proximal end 12C of the second coil sheath 12 is attached so as not to be movable rotationally about the axis with respect to the main body 40 and so as to be movable in the axial direction relatively to the main body 40 and the first coil sheath 11.

Figure 8:
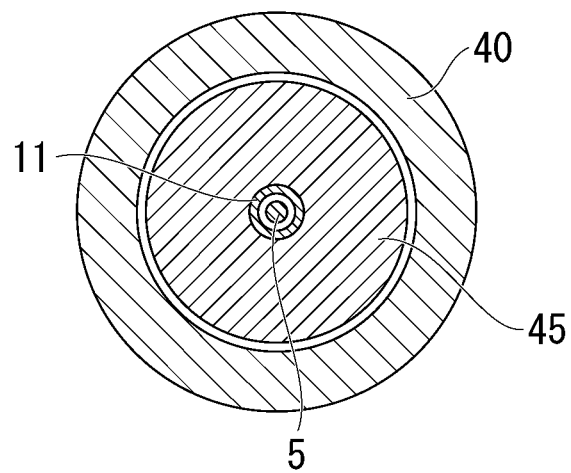
FIG. 8 is a cross sectional view taken along line B-B of FIG. 6.

FIG. 8 is a cross sectional view taken along line B-B of FIG. 6.

The locking member 45 has a substantially cylindrical shape or a ring shape, and has an outer diameter larger than the first coil sheath 11. The proximal end 11B of the first coil sheath 11 fixed to the locking member 45 is attached so as to be rotatable about the axis with respect to the main body 40 and so as not to be relatively movable in the axial direction.

Figure 9:
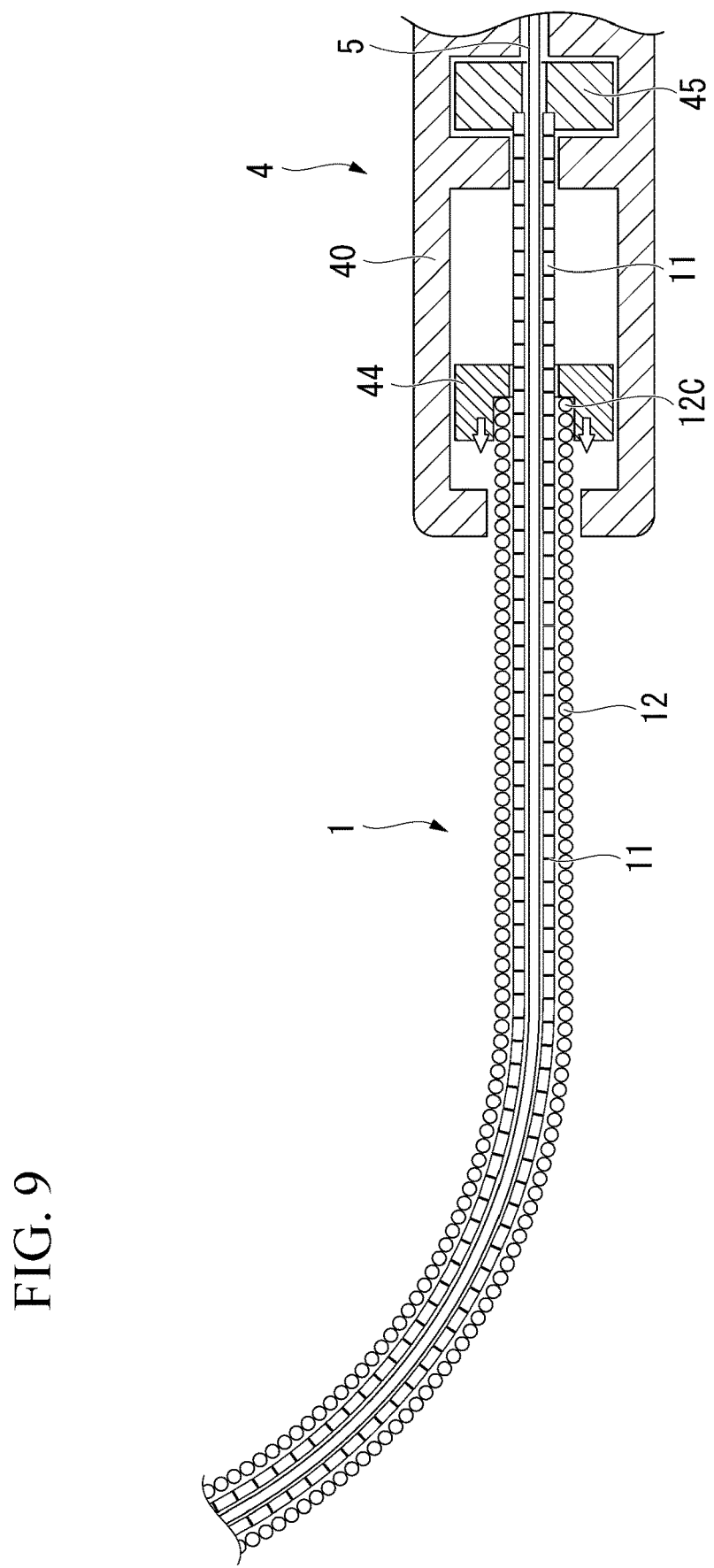
FIG. 9 is a view showing actions of the operation portion and the sheath when using the needle holder.

FIG. 9 is a view showing an action when using the operation portion 4 and the sheath 1.

According to the shape of an organ in the body cavity or the posture of a patient, meandering or bending occurs in the elongated insertion portion 202 of the flexible endoscope 200 or the sheath 1 of the needle holder 100 inserted in the insertion portion 202 in some cases. However, even in a case where the first coil sheath 11 and the second coil sheath 12, which configure the sheath 1, are relatively moved through the meandering of the sheath 1, a difference between the lengths of the first coil sheath 11 and the second coil sheath 12, which has occurred due to a relative movement of the proximal end 12C of the second coil sheath 12 relative to the first coil sheath 11 in the axial direction, is offset as the sliding member 44 connected to the proximal end 12C of the second coil sheath 12 slides in the slide groove 40g inside the main body 40 to a distal end side (a direction shown by arrows shown in FIG. 9) in the axial direction, as shown in FIG. 9.

It is preferable to set a positional relationship of the sliding member 44 in the slide groove 40g such that deflection does not occur in the sheath 1 even in a case where the sheath 1 is bent to the maximum and such that the sliding member 44 is not in contact with an end surface of the slide groove 40g in the longitudinal direction at all times.

As shown in FIG. 6, the elastic member 46 is a compression spring disposed along the axial direction of the main body 40 in which the slider 41 advances and retracts. A distal end of the elastic member 46 is attached to the main body 40 and a proximal end of the elastic member 46 is attached to the slider 41. The expanding and contracting direction of the elastic member 46 is the axial direction of the main body 40.

As shown in FIG. 3, the operation wire 5 is disposed along the longitudinal axis Y1 of the sheath 1 inside the sheath 1. The operation wire 5 is a soft wire, and can transmit an operation force from the operation portion 4.

As shown in FIG. 3, a distal end of the operation wire 5 is fixed to the first link member 36a of the link mechanism 36. As shown in FIG. 6, a proximal end of the operation wire 5 is connected to the slider 41 of the operation portion 4. That is, the distal end of the operation wire 5 and the second grasp member 32 are connected to each other via the link mechanism 36. For this reason, an operation force for operating an opening and closing operation of the second grasp member 32 with respect to the first grasp member 31 is transmitted from the operation portion 4 to the second grasp member 32 via the operation wire 5 and the link mechanism 36.

As the slider 41 advances and retracts along the main body 40, the operation wire 5 can be advanced and retracted along the longitudinal axis Y1 of the sheath 1. In the present embodiment, the operation wire 5 can be pulled to an operation portion 4 side by moving the slider 41 to the proximal end side along the main body 40.

When the engaging portion 42E and the engaged portion 40E are engaged with each other in a state where the slider 41 pulls the operation wire 5, a state where the operation wire 5 is pulled can be maintained.

As the operation wire 5 is pulled to the operation portion 4 side, the second grasp member 32 moves in a closing direction with respect to the first grasp member 31. On the other hand, as the operation wire 5 is pushed out to a grasper 3 side, the second grasp member 32 moves in an opening direction with respect to the first grasp member 31.

[Actions of Needle Holder 100]

Figure 10:
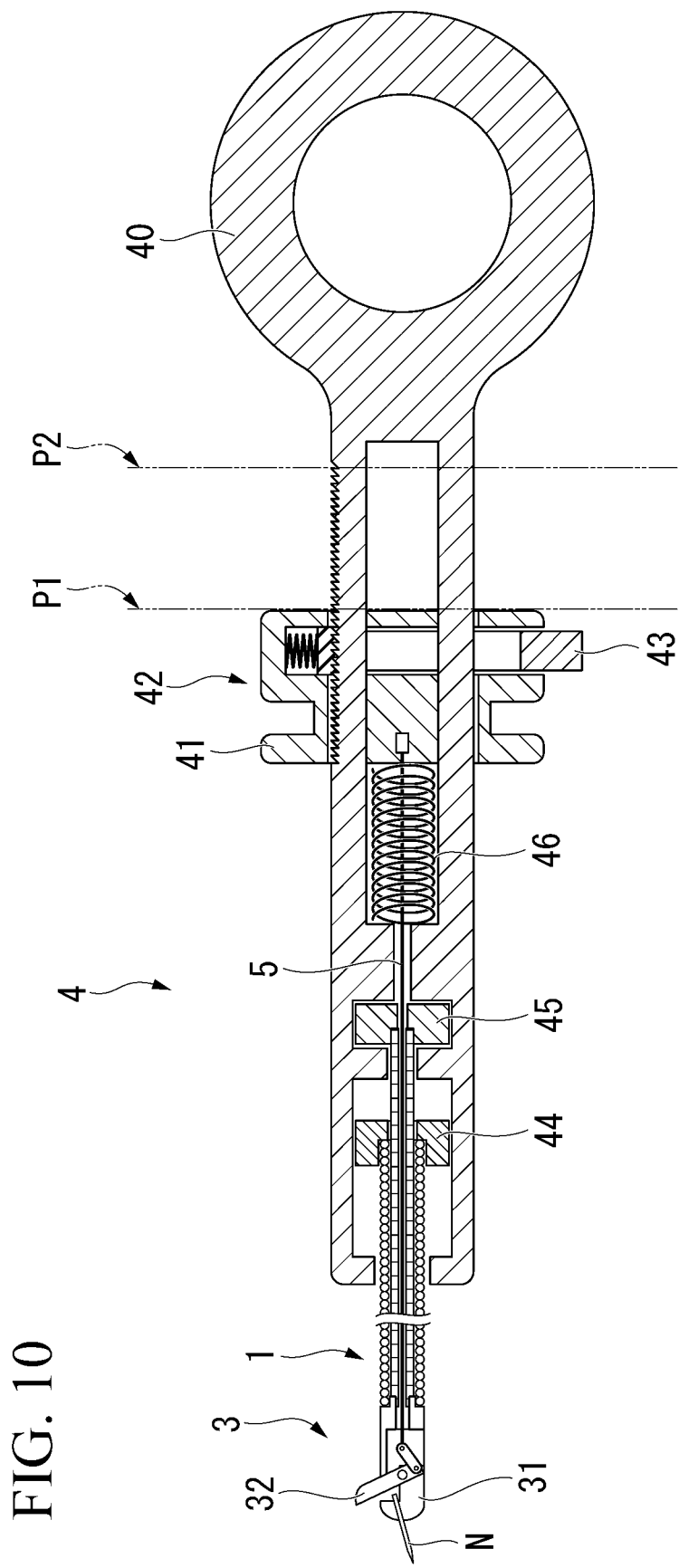
FIG. 10 is a view showing the needle holder when the grasper does not grasp a suture needle.
Figure 11:
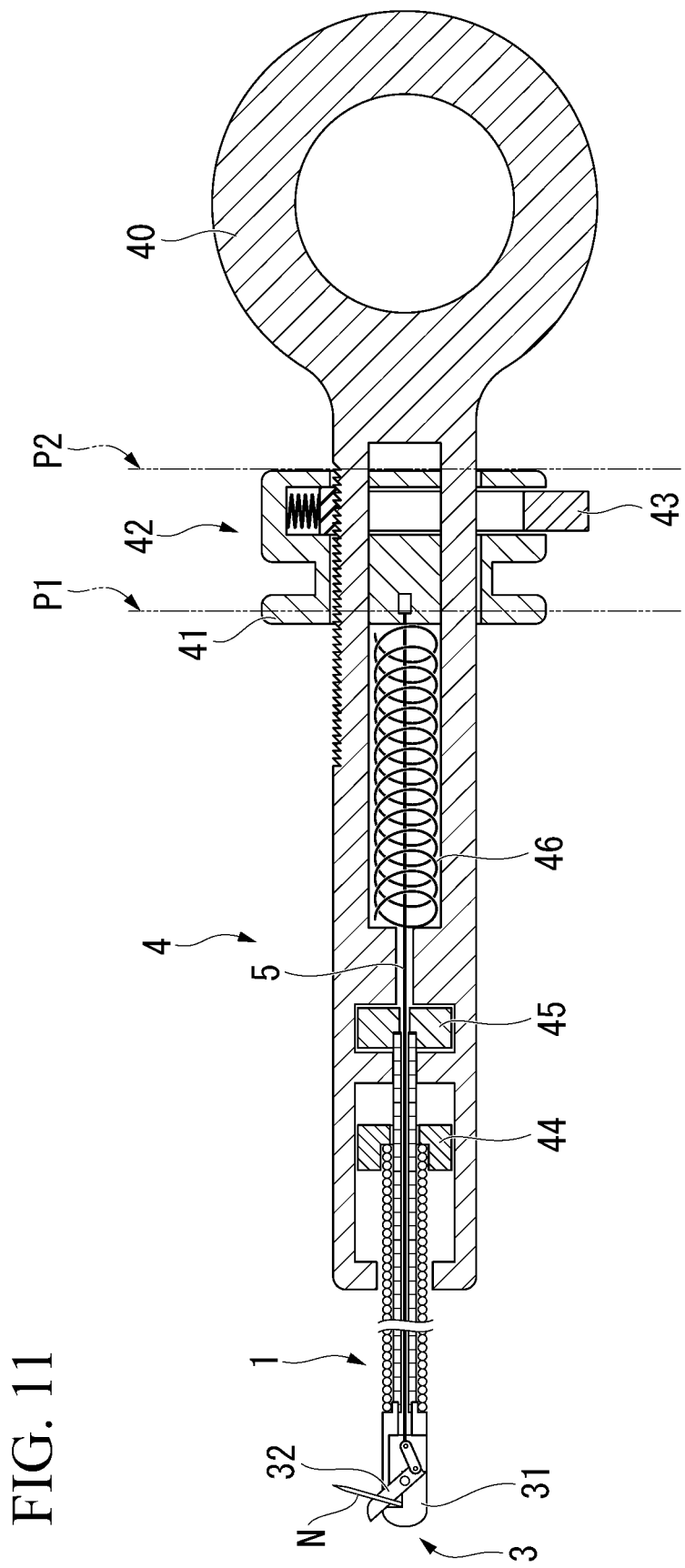
FIG. 11 is a view showing the needle holder when the grasper grasps the suture needle.
Figure 12:
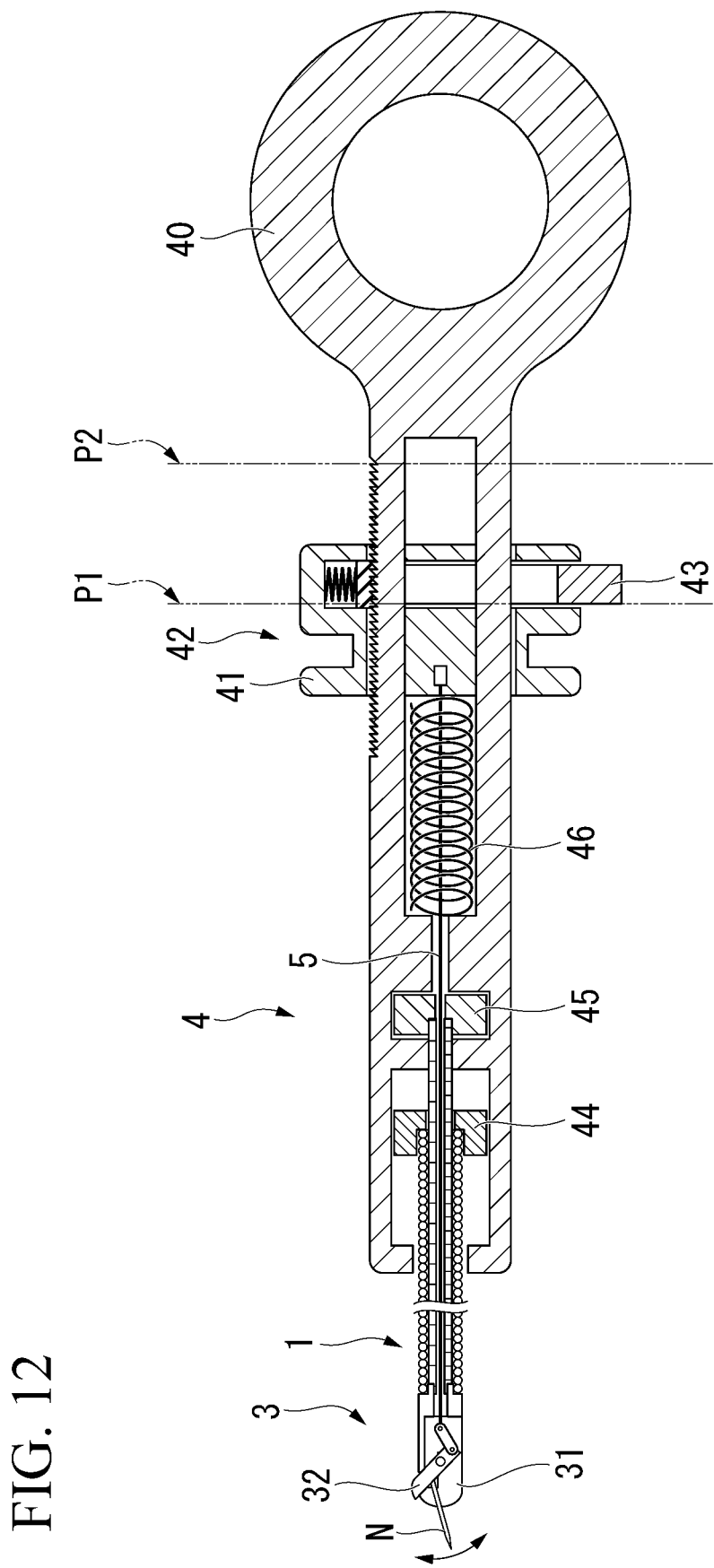
FIG. 12 is a view showing the needle holder when the grasper gently grasps the suture needle.

Next, actions of the needle holder 100 of the present embodiment will be described. FIGS. 10 to 12 are views showing the needle holder 100 when the slider 41 is advanced and retracted.

FIG. 10 is a view showing the needle holder 100 in which the grasper 3 does not grasp a suture needle N.

The surgeon advances the slider 41 along the axial direction of the main body 40 with respect to the main body 40 while maintaining a state where the release button 43 is pressed. As a result, as shown in FIG. 10, the second grasp member 32 moves in the opening direction with respect to the first grasp member 31.

As shown in FIG. 10, since the operation wire 5 is pushed with the advancement of the slider 41 and the elastic member 46 receives a compressive force in a state where the grasper 3 (the first grasp member 31 and the second grasp member 32) is opened (hereinafter, referred to as an "open state"), an elastic force generated by the elastic member 46 is larger than the tension of the operation wire 5. The elastic member 46 comes into a state of being contracted in the expanding and contracting direction from an initial state. The position of the slider 41 where the grasping state of the suture needle N by the grasper 3 is the open state will be referred to as a "first position P1". In a case where the slider 41 is moved to the first position P1, it is necessary for the surgeon to advance the slider 41 against a restoring force of the elastic member 46.

FIG. 11 is a view showing the needle holder 100 in which the grasper 3 grasps the suture needle N.

The surgeon retracts the slider 41 along the axial direction of the main body 40 with respect to the main body 40. As a result, as shown in FIG. 11, the second grasp member 32 moves in the closing direction with respect to the first grasp member 31. The suture needle N is grasped by the second grasp member 32 and the first grasp member 31 and is fixed such that the direction or position thereof cannot be changed. Specifically, the suture needle N is held so as not to be movable rotationally about a longitudinal axis of the suture needle N. A grasping force of the grasper 3 at this time will be referred to as a "first grasping force".

When the surgeon retracts the slider 41, the surgeon may maintain or may not maintain a state where the release button 43 is pressed. The surgeon can retract the slider 41 along the axial direction of the main body 40 with respect to the main body 40 regardless of a state of the release button 43.

As shown in FIG. 11, the operation wire 5 is pulled with a force larger than a restoring force generated by the elastic member 46 as the slider 41 is retracted in a state where the grasper 3 grasps the suture needle N with the first grasping force and the suture needle N is fixed so as not to be movable rotationally about the longitudinal axis of the suture needle N (hereinafter, referred to as a "first grasping state"). The elastic member 46 comes into a state of being expanded in the expanding and contracting direction from the initial state. The position of the slider 41 where the grasping state of the suture needle N by the grasper 3 is the first grasping state will be referred to as a "second position P2". It is necessary for the surgeon to move the slider 41 backward against the restoring force of the elastic member 46.

FIG. 12 is a view showing the needle holder 100 in which the grasper 3 grasps the suture needle N with a low grasping force.

The surgeon moves the slider 41 to a position between the first position P1 and the second position P2. The slider 41 is positioned as the restoring force of the elastic member 46 and the tension of the operation wire 5 are balanced. The suture needle N is grasped such that the direction or position thereof can be changed by the second grasp member 32 and the first grasp member 31. Specifically, the suture needle N is held so as to be movable rotationally about the longitudinal axis of the suture needle N. A grasping force of the grasper 3 at this time will be referred to as a "second grasping force". The second grasping force is smaller than the first grasping force.

As shown in FIG. 12, the elastic force of the elastic member 46 is balanced with the tension of the operation wire 5 in a state where the grasper 3 grasps the suture needle N with the second grasping force and the suture needle N is held so as to be movable rotationally about the longitudinal axis of the suture needle N (hereinafter, referred to as a "second grasping state"). The elastic member 46 hardly expands and contracts in the expanding and contracting direction from the initial state, and comes into a state where a restoring force is hardly generated.

The surgeon can change the direction or position of the suture needle N by moving the slider 41 to the position between the first position P1 and the second position P2 and grasping the suture needle N with the grasper 3 with a low grasping force (second grasping state). The surgeon changes the direction or position of the suture needle N, for example, by pressing the suture needle N grasped in the second grasping state against a digestive wall of a gastrointestinal tract.

Since the slider 41 is biased to move to the position between the first position P1 and the second position P2 insofar as the release button 43 is pressed even when the surgeon separates a hand from the main body 40, the grasping state of the suture needle N by the grasper 3 is the second grasping state. For this reason, the suture needle N can be prevented from falling from the grasper 3 unintentionally.

After changing the direction or position of the suture needle N to a desired direction or position, the surgeon retracts the slider 41 to the second position P2. As a result, the grasping state of the suture needle N by the grasper 3 becomes the first grasping state, and the suture needle N is fixed in a state where the direction or position thereof cannot be changed.

[Using Method of Needle Holder 100]

Next, procedures (using method) in which the needle holder 100 of the present embodiment is used will be described with reference to FIGS. 13 to 18. FIGS. 13 to 18 are views showing one process of the using method of the needle holder 100.

Before inserting the flexible endoscope 200 into the digestive tract, the surgeon makes the grasper 3 of the needle holder 100 protrude from the distal end opening portion 206a of the channel 206 of the flexible endoscope 200. The surgeon grasps the suture needle N with the grasper 3. The surgeon may grasp a suture S attached to the suture needle N with the grasper 3.

[First Step]ll

The surgeon inserts the flexible endoscope 200 from a natural opening of a patient into the digestive tract in a first step. The suture needle N or the suture S is introduced into the gastrointestinal tract in a state of being grasped by the grasper 3 protruding from the distal end opening portion 206a.

In a case where the direction or position of the suture needle N introduced in the gastrointestinal tract is not grasped in a desired direction or position, the surgeon temporarily places the suture needle N on a digestive wall T, and regrasps the suture needle N with the grasper 3. When introducing the suture needle N into the gastrointestinal tract, the suture needle N is temporarily placed on the digestive wall T, and the suture needle N is regrasped with the grasper 3 also in a case where the suture S is grasped.

Figure 13:
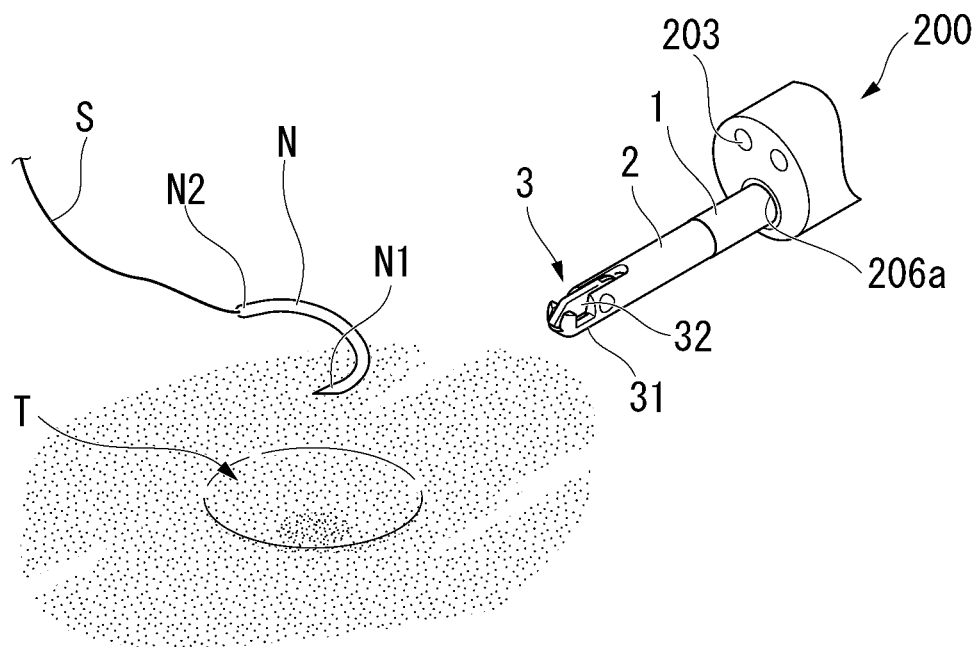
FIG. 13 is a view showing an example of a first step of grasping the suture needle with the grasper.

FIG. 13 is a view showing an example of the first step of grasping the suture needle N with the grasper 3.

Before a second step, in a state where the slider 41 is advanced to the first position P1 with respect to the main body 40 against the restoring force of the elastic member 46 (see FIG. 10), the surgeon brings the grasper 3 close to the suture needle N disposed on the digestive wall and grasps the suture needle N with the grasper 3 while observing an image captured by the imaging portion 203.

Figure 14:
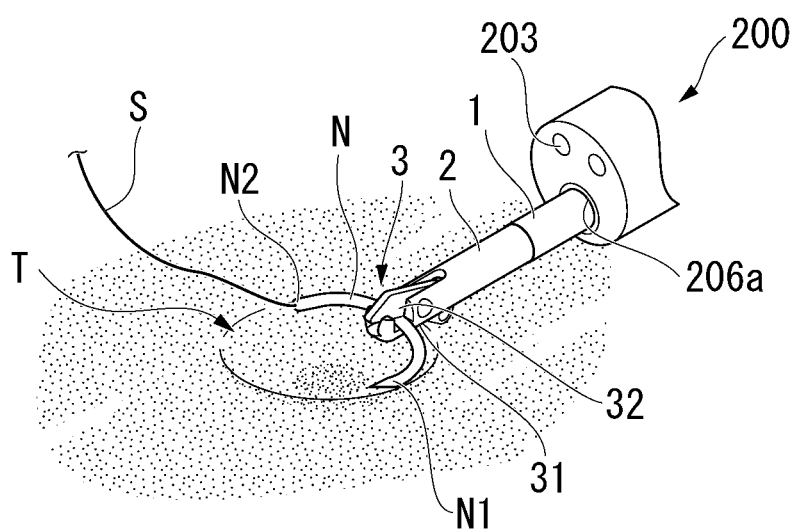
FIG. 14 is a view showing an example of the first step of grasping the suture needle in procedures by using the needle holder.

FIG. 14 is a view showing an example of the first step of grasping the suture needle N.

For example, in a state where the surgeon makes a tip end N1 and a base end N2 of the suture needle N protrude forward from the grasper 3 in the longitudinal axis Y1 of the sheath 1, the grasper 3 grasps the suture needle with the first grasping force.

[Second Step]

The surgeon adjusts the grasping force of the grasper 3 that grasps the suture needle N positioned inside a luminal organ (gastrointestinal tract) in the second step. Specifically, the grasper 3 grasps the suture needle with the second grasping force by retracting the slider 41 to the position between the first position P1 and the second position P2 with respect to the main body 40 with the restoring force of the elastic member 46 (see FIG. 12). The grasping state of the suture needle N by the grasper 3 becomes the second grasping state. In the second step, the restoring force of the elastic member 46 and the tension of the operation wire 5 are balanced, the slider 41 is positioned, and the suture needle N is grasped by the grasper 3.

[Third Step]

After adjusting the grasping force of the grasper 3 that grasps the suture needle N into the second grasping force, the surgeon changes the direction of a tip of the suture needle N while pressing a part of the suture needle N against the digestive wall T in a state where the suture needle N is grasped by the grasper 3 in a third step.

Figure 15:
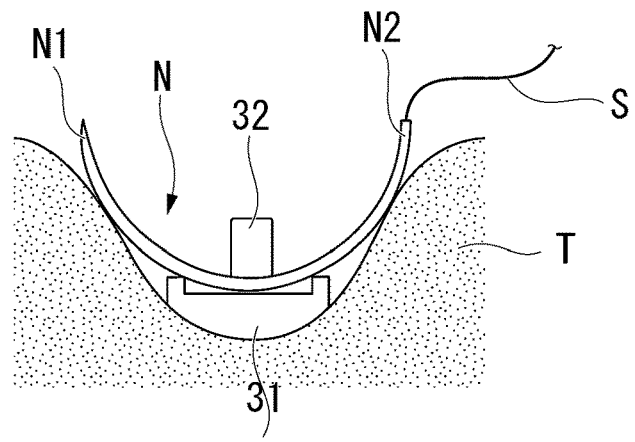
FIG. 15 is a front view of the grasper, which shows an example of a third step in the procedures in which the needle holder is used.

FIG. 15 is a front view of the grasper 3, which shows an example of the third step.

In a state where the suture needle N is grasped by the grasper 3 with the second grasping force, the surgeon adjusts the direction of the tip end of the suture needle N while pressing at least one of the tip end N1 and the base end N2 of the suture needle N against the digestive wall T. A part of the digestive wall T against which the suture needle is pressed is not limited insofar as it is a wall of the gastrointestinal tract. In an example of the third step shown in FIG. 15, there is a transition from a state where an intermediate portion of the suture needle N is grasped by the grasper 3 and the suture needle N is aligned in a tangential direction of a surface of the digestive wall T (see FIG. 14) to a state where the tip end of the suture needle N is directed in a direction substantially perpendicular to the surface of the digestive wall T while pressing two places including a tip end N1 side and a base end N2 side of the suture needle N against the digestive wall T.

Figure 16:
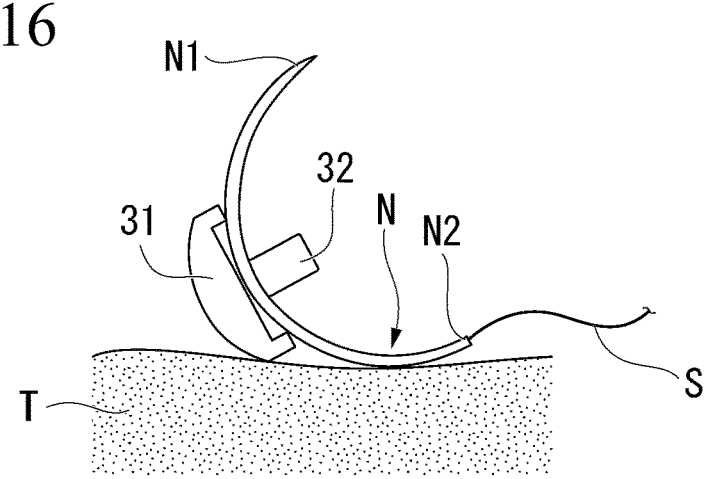
FIG. 16 is a front view of the grasper, which shows another example of the third step.

FIG. 16 is a front view of the grasper 3, which shows another example of the third step.

In the example of the third step shown in FIG. 16, the intermediate portion of the suture needle N is grasped by the grasper 3, and the direction of the tip of the suture needle N is adjusted while pressing one place which is the base end N2 side of the suture needle N against the digestive wall T.

Figure 17:
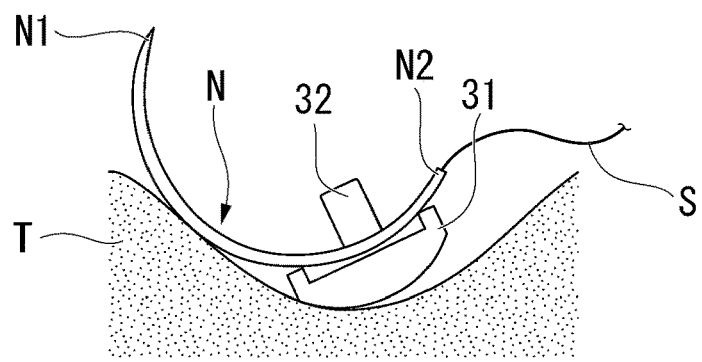
FIG. 17 is a front view of the grasper, which shows still another example of the third step.

FIG. 17 is a front view of the grasper 3, which shows still another example of the third step.

A place where the grasper 3 grasps the suture needle N does not matter in the third step. As shown in FIG. 17, in a case where the base end N2 side of the suture needle N is grasped by the grasper 3, the direction of the tip end of the suture needle N is adjusted while pressing the intermediate portion between the tip end N1 side or the tip end N1 and the base end N2 of the suture needle N against the digestive wall T.

[Fourth Step]

Figure 18:
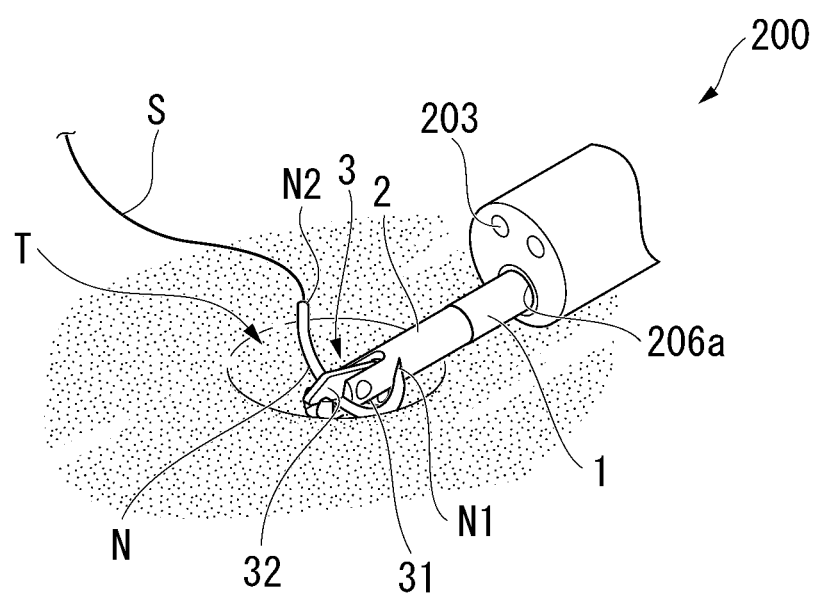
FIG. 18 is a view showing an example of a fourth step in the procedures by using the needle holder.

FIG. 18 is a view showing an example of a fourth step.

After adjusting the direction of the tip end of the suture needle N, by retracting the slider 41 to the second position P2 with respect to the main body 40 against the restoring force of the elastic member 46, the suture needle N is grasped by the grasper 3 with the first grasping force (see FIG. 11). As shown in FIG. 18, the grasping state of the suture needle N by the grasper 3 becomes the first grasping state.

After fixing the direction or position of the suture needle N to a desired direction or position, the surgeon sutures the treatment target. In a case of further changing the direction or position of the suture needle N, the surgeon performs the second step to the fourth step again.

In the needle holder for an endoscope 100 according to the present embodiment, in suturing work under the flexible endoscope, the direction or position of the suture needle N can be easily changed to a desired direction or position by adjusting a force of grasping the suture needle N. The surgeon can easily change the direction or position of the suture needle N by moving the slider 41 to the position between the first position P1 and the second position P2 and bringing the grasping state of the suture needle N by the grasper 3 to the second grasping state.

In the procedures (using method) in which the needle holder for an endoscope 100 according to the present embodiment is used, the surgeon can easily change the direction or position of the suture needle N by pressing the suture needle N in the second grasping state against the digestive wall of the gastrointestinal tract.

Although the present embodiment has been described in detail with reference to the drawings hereinbefore, a specific configuration is not limited to this embodiment, and includes design changes without departing from the gist of the present disclosure. In addition, it is possible to combine and configure components shown in the embodiment described above and modified examples as appropriate.

Although the operation portion 4 has the fixing mechanism 42, which is the ratchet mechanism in the embodiment, the form of the operation portion is not limited thereto. The operation portion may not have the fixing mechanism 42.

Figure 19:
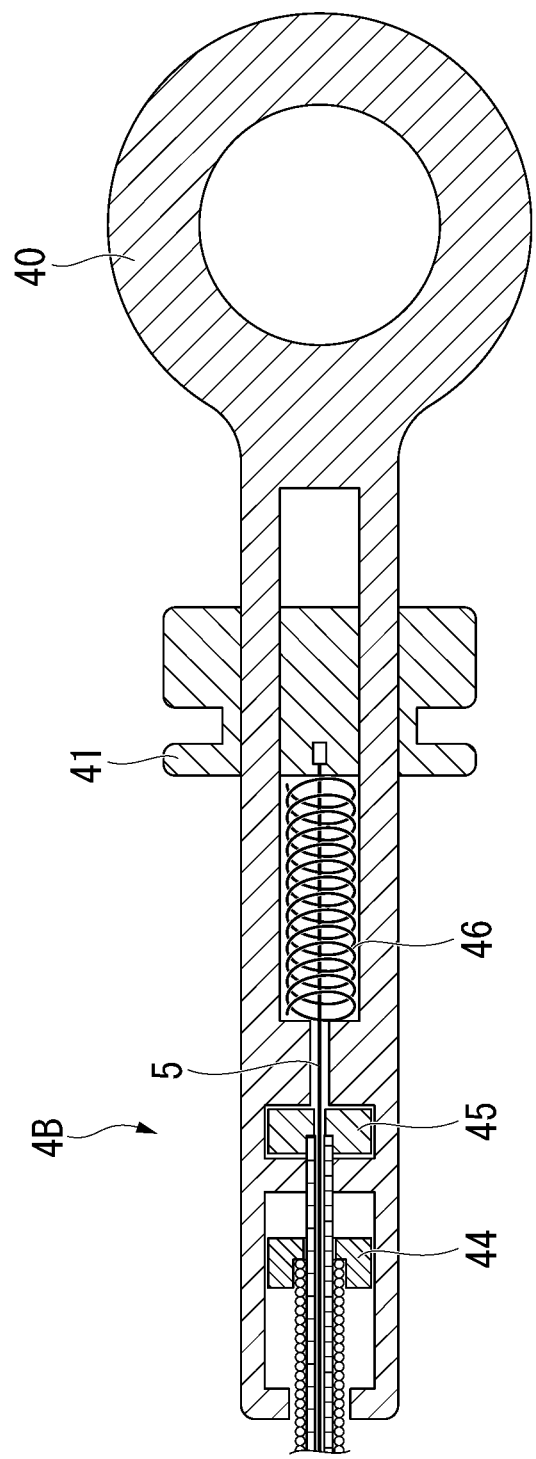
FIG. 19 is a view showing a modified example of the operation portion of the needle holder.

FIG. 19 is a view showing an operation portion 4B, which is a modified example of the operation portion 4. Even in a case where an operation portion does not have the fixing mechanism 42 like the operation portion 4B, the slider 41 is biased to move to the position between the first position P1 and the second position P2. Thus, the grasping state of the suture needle N by the grasper 3 becomes the second grasping state in a case where the surgeon has separated the hand from the slider 41.

Modified Example 2

Figure 20:
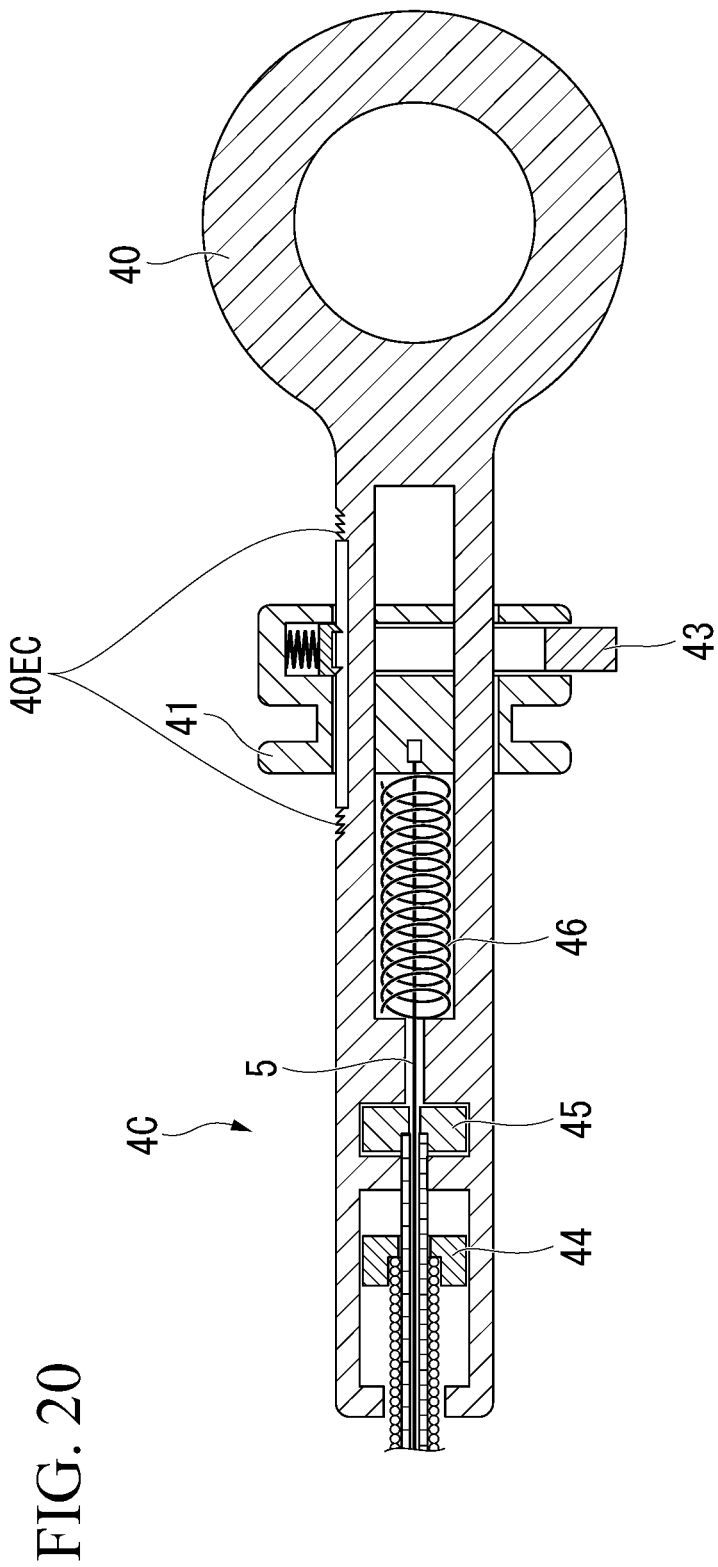
FIG. 20 is a view showing another modified example of the operation portion of the needle holder.
Figure 21:
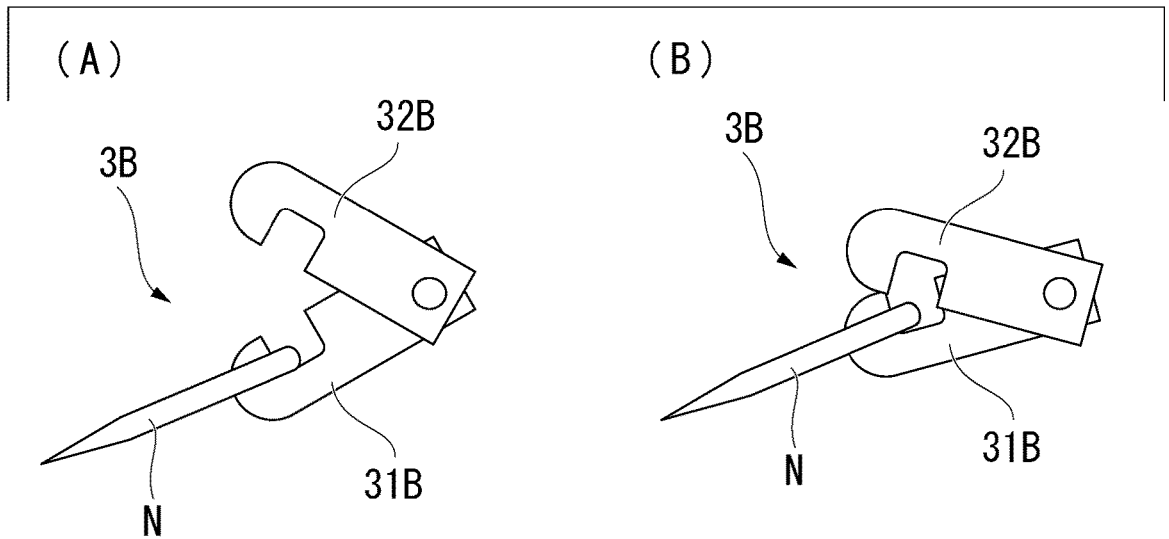
FIG. 21 is a view showing still another modified example of the grasper of the needle holder.
Figure 22:
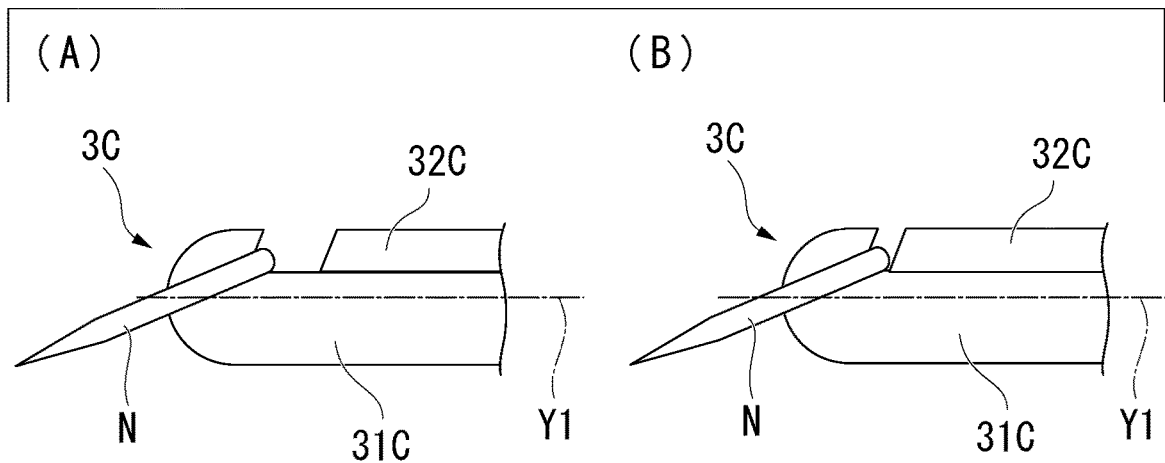
FIG. 22 is a view showing still another modified example of the grasper of the needle holder.
Figure 23:
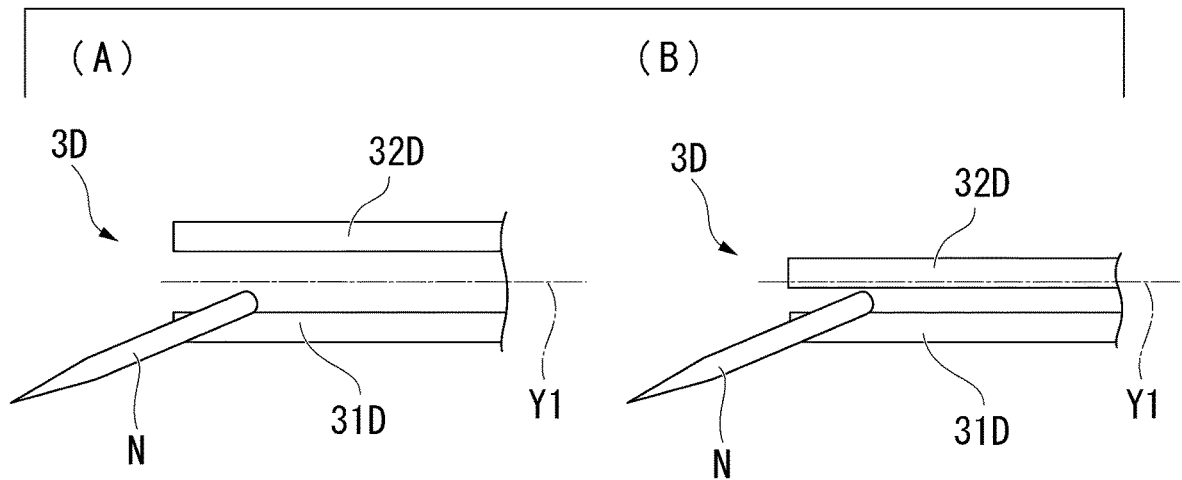
FIG. 23 is a view showing still another modified example of the grasper of the needle holder.
Figure 24:
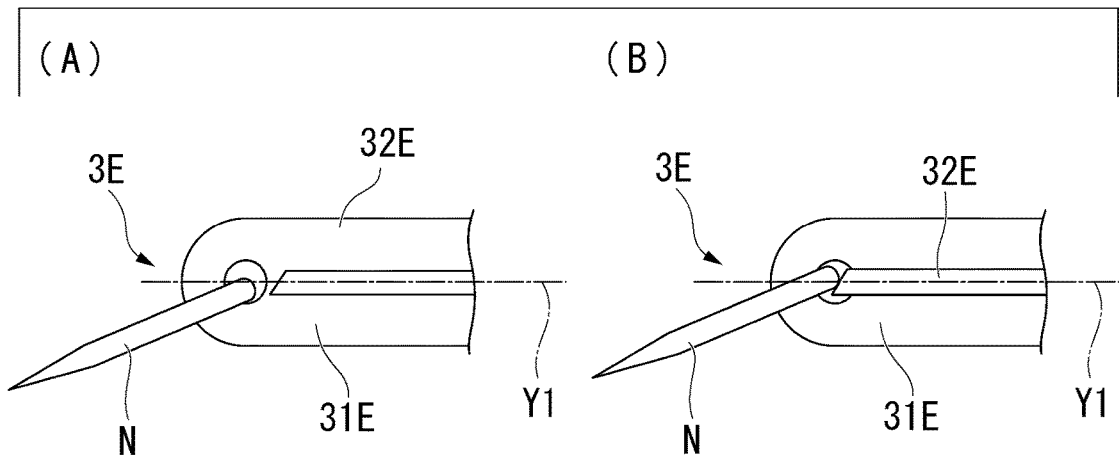
FIG. 24 is a view showing still another modified example of the grasper of the needle holder.

Although the engaged portion 40E is provided at the main body 40 in the entire area in a range where the slider 41 advances and retracts in the embodiment, the form of the engaged portion is not limited thereto. The engaged portion may be provided only at a part of the range where the slider 41 advances and retracts. FIG. 20 is a view showing an operation portion 4C, which is a modified example of the operation portion 4. Like an engaged portion 40EC of the operation portion 4C, an engaged portion may be provided in a range of engaging with the engaging portion 42E only in a case where the slider 41 is at the first position P1 and the second position P2.

Modified Example 3

Although the grasper 3 grasps the suture needle N as the second grasp member 32 opens and closes with respect to the first grasp member 31 in the embodiment, the form of the grasper is not limited thereto. FIGS. 21 to 24 show modified examples of the grasper. FIGS. 21A, 22A, 23A, and 24A show the grasper of which the grasping state is the open state. FIGS. 21B, 22B, 23B, and 24B show the grasper of which the grasping state is the second grasping state.

A grasper 3B, which is a modified example of the grasper shown in FIGS. 21A and 21B, grasps the suture needle N as both of a first grasp member 31B and a second grasp member 32B open and close.

A grasper 3C, which is a modified example of the grasper shown in FIGS. 22A and 22B, grasps the suture needle N as a second grasp member 32C advances and retracts along the longitudinal axis Y1 with respect to a first grasp member 31C.

A grasper 3D, which is a modified example of the grasper shown in FIG. 23B, grasps the suture needle N as a second grasp member 32D performs a pantograph operation along a direction perpendicular to the longitudinal axis Y1 with respect to a first grasp member 31D.

A grasper 3E, which is a modified example of the grasper shown in FIGS. 24A and 24B, has a through-hole 31H, through which the suture needle N can pass, in a first grasp member 31E. The grasper 3E grasps the suture needle N as a second grasp member 32E advances and retracts along the longitudinal axis Y1 in a state where the suture needle N has passed through the through-hole 31H.

Modified Example 4

Figure 25:
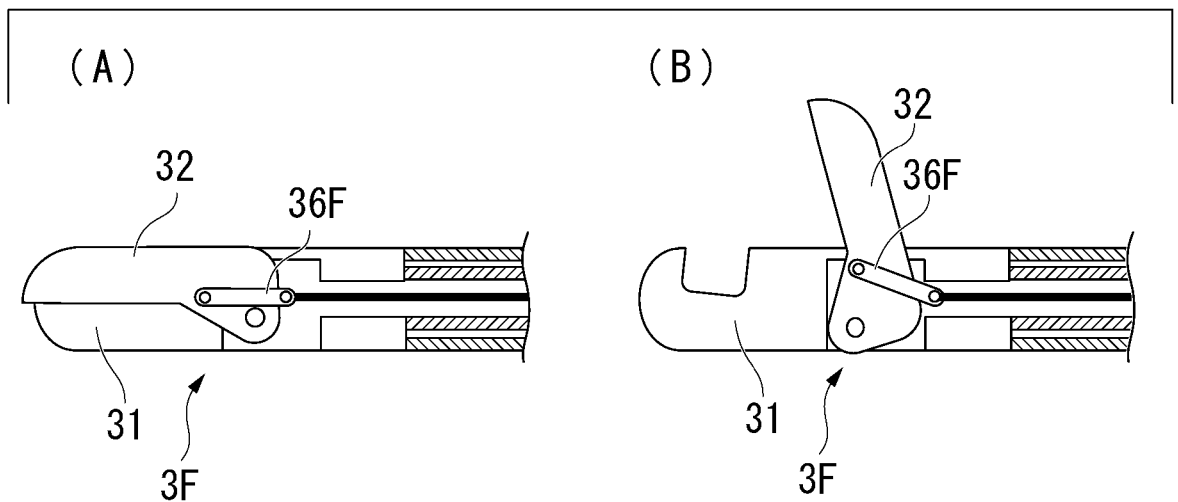
FIG. 25 is a view showing still another modified example of the grasper of the needle holder.
Figure 26:
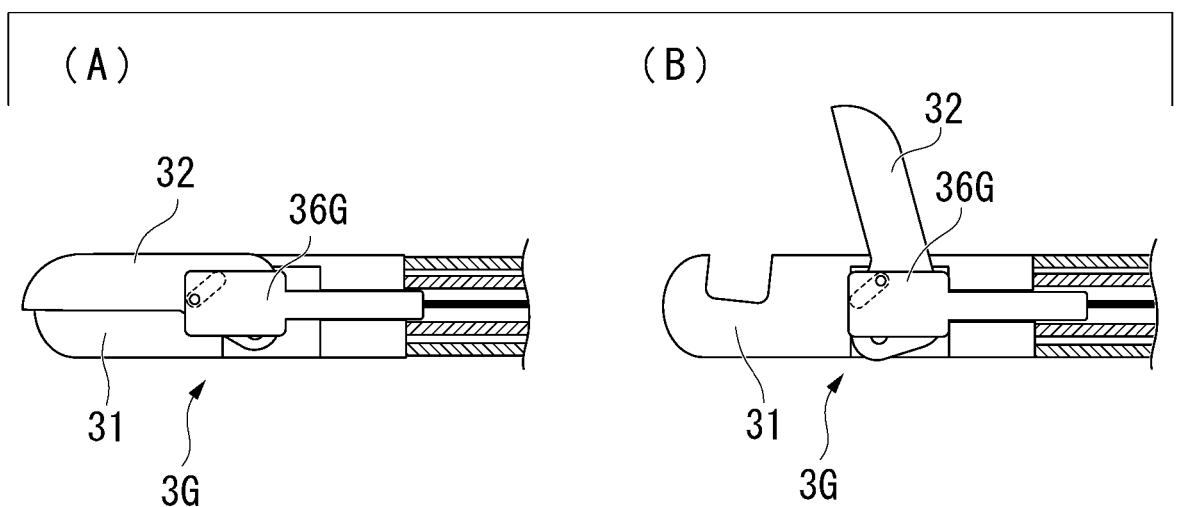
FIG. 26 is a view showing still another modified example of the grasper of the needle holder.

Although the second grasp member 32 moves in the closing direction with respect to the first grasp member 31 as the operation wire 5 is pulled to the operation portion 4 side in the embodiment, the form of the grasper 3 is not limited thereto. FIGS. 25A to 26B show modified examples of the grasper. FIGS. 25A and 26A show the grasper in a closed state. FIGS. 25B and 26B show the grasper in an open state.

Like a grasper 3F, which is a modified example of the grasper shown in FIGS. 25A, and 25B, a grasper may have a link mechanism 36F in which the second grasp member 32 moves in the opening direction with respect to the first grasp member 31 as the operation wire 5 is pulled to the operation portion 4 side.

Like a grasper 3G, which is a modified example of the grasper shown in FIGS. 26A and 26B, a grasper may have a cam mechanism 36G in which the second grasp member 32 moves in the opening direction with respect to the first grasp member 31 as the operation wire 5 is pulled to the operation portion 4 side.

Figure 27:
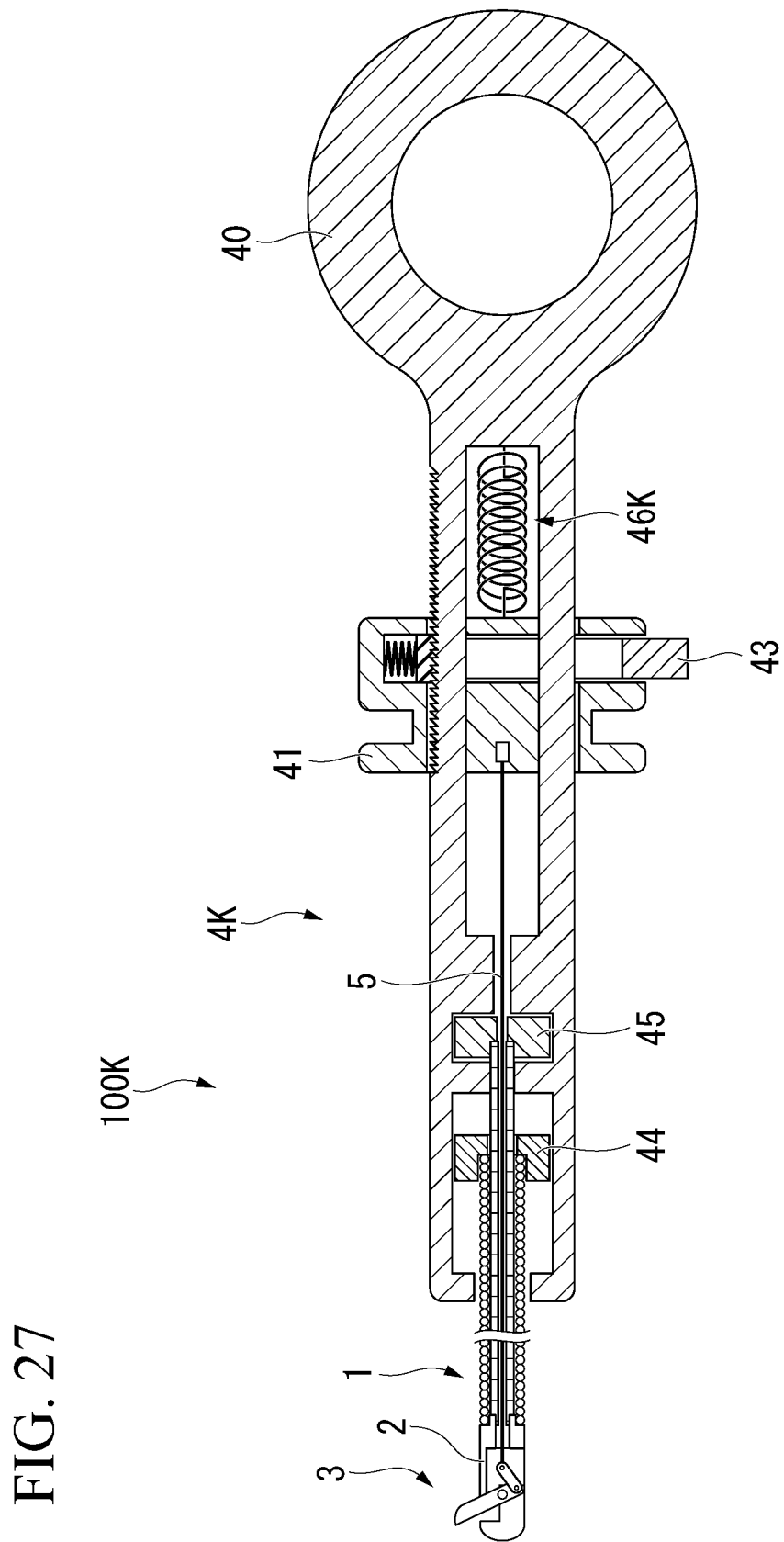
FIG. 27 is a view showing a needle holder according to an exemplary embodiment.

A needle holder 100K according to another exemplary embodiment of the present disclosure will be described with reference to FIG. 27. In the following description, configurations common to the previous description will be assigned the same reference signs, and a description thereof will be omitted. FIG. 27 is a view showing the needle holder 100K.

The needle holder 100K has the sheath 1, the hard portion 2, the grasper 3, an operation portion 4K, and the operation wire 5 inserted through the sheath 1.

The operation portion 4K has the main body 40, the slider 41, the fixing mechanism 42, the release button 43, the sliding member 44, the locking member 45, and an elastic member 46K.

The elastic member 46K is a tension spring disposed along the axial direction of the main body 40 in which the slider 41 advances and retracts, and has a distal end attached to the slider 41 and a proximal end attached to the main body 40. The expanding and contracting direction of the elastic member 46K is the axial direction of the main body 40. The elastic member 46K may be a plurality of tension springs. In addition, the elastic member 46K may not necessarily be a compression spring, and may be an elastic body that generates an elastic force between the slider 41 and the main body 40.

Since the operation wire 5 is pushed with the advancement of the slider 41 and the elastic member 46K receives a pulling force in a state where the grasper 3 is opened, the elastic force of the elastic member 46K is larger than the tension of the operation wire 5.

As the slider 41 is retracted when the grasping state of the suture needle N by the grasper 3 is in the first grasping state, the operation wire 5 is pulled with a force larger than the restoring force generated by the elastic member 46K.

When the grasping state of the suture needle N by the grasper 3 is in the second grasping state, the elastic force of the elastic member 46K is balanced with the tension of the operation wire 5.

In the needle holder 100K according to the present embodiment, like the needle holder 100 of the above embodiment described with respect to FIGS. 1-18, in suturing work under the flexible endoscope, the direction or position of the suture needle N can be easily changed to a desired direction or position by adjusting the force of grasping the suture needle N.

Although the present embodiment has been described in detail with reference to the drawings hereinbefore, a specific configuration is not limited to this embodiment, and includes design changes without departing from the gist of the present disclosure. In addition, it is possible to combine and configure components shown in the embodiments described above and modified examples as appropriate.

What is claimed is:

1. An operating method of a suture needle comprising:
introducing the suture needle into a luminal organ through a natural opening in a state that the suture needle is grasped by a grasper that is a part of a needle holder;
adjusting a grasping force of the grasper, which grasps the suture needle positioned inside the luminal organ; and
changing a direction of a tip of the suture needle while pressing a part of the suture needle positioned inside the luminal organ against an interior surface of the luminal organ in a state in which the suture needle is held by the grasper so as to be rotatable around a longitudinal axis of the suture needle with respect to the grasper without being released by the grasper,
wherein the changing of the direction of the tip of the suture needle includes transitioning the suture needle from a state of being aligned with a tangential direction of the interior surface of the luminal organ to a state of being directed in a direction intersecting the interior surface of the luminal organ, in a state where the needle holder is aligned with the tangential direction of the interior surface of the luminal organ.

2. The operating method according to claim 1, wherein:
the needle holder is inserted into an endoscope and is introduced into the luminal organ together with the suture needle; and
the direction of the tip of the suture needle is changed after the grasping force of the grasper is adjusted.

3. The operating method according to claim 2, wherein:
the needle holder further includes an operation wire connected to the grasper, and an elastic member that is configured to elastically deform depending on an opening and closing position of the grasper, and
the adjusting of the grasping force includes balancing a restoring force of the elastic member with a tension of the operation wire in a state in which the suture needle is grasped by the grasper.

4. The operating method according to claim 3, wherein:
the needle holder further comprises a sheath and an operation portion configured to open and close the grasper,
the operation portion includes:
a main body that extends along a longitudinal axis, and is fixed to a proximal end portion of the sheath; and
a slider attached to the main body so as to be slidable along the longitudinal axis with respect to the main body,
the elastic member is positioned between the main body and the slider,
a distal end of the operation wire is connected to the grasper,
a proximal end of the operation wire is connected to the slider, and
the adjusting of the grasping force further includes positioning the slider along the longitudinal axis of the main body to balance the restoring force of the elastic member with the tension of the operation wire in the state in which the suture needle is grasped by the grasper.

5. The operating method according to claim 3, wherein:
the needle holder further comprises a sheath and an operation portion configured to open and close the grasper,
the operation portion includes:
a main body that extends along a longitudinal axis, and is fixed to a proximal end portion of the sheath; and
a slider attached to the main body so as to be slidable along the longitudinal axis with respect to the main body,
the elastic member is positioned between the main body and the slider,
a distal end of the operation wire is connected to the grasper,
a proximal end of the operation wire is connected to the slider,
the operating method further comprises:
releasing grasping of the suture needle in response to an operation of advancing the slider to a first position with respect to the main body against the restoring force of the elastic member; and
grasping the suture needle with a first grasping force in response to an operation of retracting the slider to a second position with respect to the main body against the restoring force of the elastic member; and
the adjusting of the grasping force includes adjusting the grasping force from the first grasping force to a second grasping force smaller than the first grasping force by positioning the slider between the first position and the second position such that the restoring force of the elastic member is balanced with the tension of the operation wire.

6. The operating method according to claim 5, wherein:
the adjusting of the grasping force includes advancing the slider with respect to the main body with restoration of the elastic member in a state in which the suture needle is grasped by the grasper with the second grasping force such that a tip end and a base end of the suture needle protrude from the grasper, and
the direction of the tip end of the suture needle is changed while pressing the tip end and the base end of the suture needle against the interior surface of the luminal organ in a state where the grasper grasps the suture needle with the second grasping force.

7. The operating method according to claim 5, wherein:
the releasing of the grasping of the suture needle includes releasing the suture needle onto the interior surface of the luminal organ, and
the grasping of the suture needle includes bringing the grasper close to the suture needle disposed on the interior surface of the luminal organ, and grasping the suture needle disposed on the interior surface of the luminal organ by the grasper.

8. The operating method according to claim 6, further comprising:
adjusting the grasping force from the second grasping force to the first grasping force by retracting the slider to the second position with respect to the main body against the restoring force of the elastic member, after the direction of the tip of the suture needle is changed.

9. An operating method of a suture needle comprising:
introducing the suture needle into a luminal organ in a state that the suture needle is grasped by a needle holder;
adjusting a grasping force of the needle holder, which grasps the suture needle positioned inside the luminal organ; and
while pressing a part of the suture needle positioned inside the luminal organ against an interior surface of the luminal organ, transitioning a tip end of the suture needle from a state of being directed with a tangential direction of the interior surface of the luminal organ to a state of being directed in a direction intersecting the interior surface of the luminal organ, the transitioning being performed in a state in which the suture needle is held by the needle holder so as to be rotatable around a longitudinal axis of the suture needle with respect to the needle holder without being released by the needle holder.

10. The operating method according to claim 9, wherein:
the needle holder further includes a grasper that grasps the suture needle, an operation wire connected to the grasper, and an elastic member that is configured to elastically deform depending on an opening or closing position of the grasper, and
the adjusting of the grasping force of the needle holder comprises adjusting the grasping force of the grasper including balancing a restoring force of the elastic member with a tension of the operation wire in a state in which the suture needle is grasped by the grasper.

11. The operating method according to claim 9, wherein:
the needle holder further includes a grasper that grasps the suture needle, an operation wire connected to the grasper, and an elastic member that is configured to elastically deform depending on an opening or closing position of the grasper, and
the transitioning of the tip end of the suture needle includes changing of the direction of the tip end of the suture needle in a state of balancing a restoring force of the elastic member with a tension of the operation wire in a state in which the suture needle is grasped by the grasper.

12. The operating method according to claim 9, wherein:
the needle holder further includes a grasper that grasps the suture needle, an operation wire connected to the grasper, and an elastic member that is configured to elastically deform depending on an opening or closing position of the grasper, and
the transitioning of the tip end of the suture needle includes changing of the direction of the tip end of the suture needle by pressing the tip end and a base end of the suture needle against the interior surface of the luminal organ in a state of balancing a restoring force of the elastic member with a tension of the operation wire in a state in which the suture needle is grasped by the grasper.

13. The operating method according to claim 1, wherein:
the needle holder is inserted into an endoscope and is introduced into the luminal organ together with the suture needle,
the needle holder includes an operation wire connected to the grasper, and an elastic member that is configured to elastically deform depending on an opening or closing position of the grasper, and
the direction of the tip of the suture needle is changed in a state of balancing a restoring force of the elastic member with a tension of the operation wire in the state in which the suture needle is grasped by the grasper.

14. The operating method according to claim 1, wherein:
the needle holder is inserted into an endoscope and is introduced into the luminal organ together with the suture needle,
the needle holder includes an operation wire connected to the grasper, and an elastic member that is configured to elastically deform depending on an opening or closing position of the grasper, and
the direction of the tip of the suture needle is changed by pressing the tip and a base end of the suture needle against a wall of the luminal organ in a state of balancing a restoring force of the elastic member with a tension of the operation wire in the state in which the suture needle is grasped by the grasper.

15. The operating method according to claim 1, wherein:
the grasping force is adjusted from a first grasping force to a second grasping force that is lower than the first grasping force;
in a state where the grasper grasps the suture needle with the first grasping force, the suture needle is held so as to not be rotatable around the longitudinal axis of the suture needle with respect to the grasper; and
in a state where the grasper grasps the suture needle with the second grasping force, the suture needle is held by the grasper so as to be rotatable around the longitudinal axis of the suture needle with respect to the grasper without being released by the grasper.

16. The operating method according to claim 9, wherein:
the grasping force is adjusted from a first grasping force to a second grasping force that is lower than the first grasping force;
in a state where the needle holder grasps the suture needle with the first grasping force, the suture needle is held so as to not be rotatable around the longitudinal axis of the suture needle with respect to the needle holder; and
in a state where the needle holder grasps the suture needle with the second grasping force, the suture needle is held by the needle holder so as to be rotatable around the longitudinal axis of the suture needle with respect to the needle holder without being released by the needle holder.

17. The operating method according to claim 1, wherein the direction of the tip of the suture needle is changed while pressing the part of the suture needle positioned inside the luminal organ against the interior surface of the luminal organ without penetrating the interior surface of the luminal organ.

18. The operating method according to claim 9, wherein the tip end of the suture needle is transitioned from the state of being directed with the tangential direction of the interior surface of the luminal organ to the state of being directed in the direction intersecting the interior surface of the luminal organ without penetrating the interior surface of the luminal organ.

19. The operating method according to claim 1, wherein the direction of the tip of the suture needle is changed by rotating the suture needle around the longitudinal axis of the suture needle without changing a shape of the suture needle.

20. The operating method according to claim 9, wherein the transitioning of the tip end of the suture needle includes rotating the suture needle around the longitudinal axis of the suture needle without changing a shape of the suture needle.

* * * * *